(12) United States Patent
Yoshida et al.

(10) Patent No.: US 9,139,866 B2
(45) Date of Patent: *Sep. 22, 2015

(54) METHOD FOR DETECTION OF MICROORGANISM AND KIT FOR DETECTION OF MICROORGANISM

(75) Inventors: Shinichi Yoshida, Fukuoka (JP); Takashi Soejima, Zama (JP)

(73) Assignee: MORINAGA MILK INDUSTRY CO., LTD., Tokyo (JP)

( * ) Notice: Subject to any disclaimer, the term of this patent is extended or adjusted under 35 U.S.C. 154(b) by 859 days.

This patent is subject to a terminal disclaimer.

(21) Appl. No.: 11/994,823

(22) PCT Filed: Feb. 17, 2006

(86) PCT No.: PCT/JP2006/302893
§ 371 (c)(1),
(2), (4) Date: Jan. 4, 2008

(87) PCT Pub. No.: WO2007/094077
PCT Pub. Date: Aug. 23, 2007

(65) Prior Publication Data
US 2009/0305240 A1    Dec. 10, 2009

(51) Int. Cl.
*C12Q 1/68* (2006.01)
*C07H 21/04* (2006.01)
*C07H 21/02* (2006.01)

(52) U.S. Cl.
CPC .............. *C12Q 1/6806* (2013.01); *C12Q 1/686* (2013.01); *C12Q 1/689* (2013.01); *C12Q 1/6888* (2013.01); *C12Q 2600/158* (2013.01)

(58) Field of Classification Search
CPC ............. C12Q 1/686; C12Q 2521/519; C12Q 1/6888; C12Q 1/689
See application file for complete search history.

(56) References Cited

U.S. PATENT DOCUMENTS 8,221,975 B2 *    7/2012    Yoshida et al. ............... 435/6.1
2004/0110247 A1 *   6/2004    Moreillon et al. ............. 435/32

FOREIGN PATENT DOCUMENTS

| EP | 0 337 896 | 10/1989 |
|---|---|---|
| JP | 2003-530118 | 10/2003 |
| WO | WO 97/48822 | 12/1997 |
| WO | WO 01/77379 | 10/2001 |
| WO | WO 02/052034 | 7/2002 |
| WO | WO 2004/015141 | 2/2004 |

OTHER PUBLICATIONS

Rudi et al. Use of ethidium monoazide and PCR in combination for quantification of viable and dead cells in complex samples. Applied and Environmental Microbiology (2005) 71(2): 1018-1024.*

Hong et al. Application of oligonucleotide array technology for the rapid detection of pathogenic bacteria of foodborne infections. Journal of Microbiological Methods (2004) 58: 403-411.*

Eliopoulos et al. In Vitro Activity of Ciprofloxacin, a New Carboxyquinoline Antimicrobial Agent. Antimicrobial Agents and Chemotherapy (1984) 25(3): 331-335.*

Chakraborty et al. DNA topoisomerase inhibitors: potential uses in molecular medicine. Expert Review on Therapeutic Patents (1994) 4(6): 655-668.*

Wesche et al. Stress, sublethal injury, resuscitation, and virulence of bacterial foodborne pathogens. J Food Protection 2009;72(5):1121-38.*

Wasserman, R.A. et al., J. Biol. Chem., vol. 269, pp. 20943-20951 (1994).*

Besnard, V. et al., Lett. Appl. Microbiol., vol. 31, pp. 77-81 (2000).*

Rudi, et al. "Detection of Viable and Dead *Listeria monocytogenes* on Gouda-Like Cheeses by Real-Time PCR," *Letters in Applied Microbiology*, vol. 40, No. 4, pp. 301-306, 2005.

Rudi, et al. "Use of Ethidium Monoazide and PCR in Combination for Quantification of Viable and Dead Cells in Complex Samples," *Applied and Environmental Microbiology*, vol. 71, No. 2, pp. 1018-1024, 2005.

Mengaud, et al. "Expression in *Escherichia coli* and Sequence Analysis of the Listeriolysin O Determinant of *Listeria monocytogenes*," *Infection and Immunity*, vol. 56, No. 4, pp. 766-772, 1988.

Marx, et al. "Covalent Attachment of Ethidium to DNA Results in Enhanced Topoisomerase II-Mediated DNA Cleavage," *Biochemistry*, vol. 36, No. 50., pp. 15884-15891, 1997.

Mukherjee, et al. "Ciprofloxacin: Mammalian DNA Topoisomerase Type II Poison In Vivo," *Mutation Research*, vol. 301, No. 2, pp. 87-92, 1993.

International Search Report dated Mar. 30, 2006.

Elsea, et al. "Quinolones Share a Common Interaction Domain on Topoisomerase II with Other DNA Cleavage-Enhancing Antineoplastic Drugs," *Biochemistry*, vol. 36, No. 10, pp. 2919-2924, 1997.

Nogva, et al. "Application of 5'-Nuclease PCR for Quantitative Detection of *Listeria monocytogenes* in Pure Cultures, Water, Skim Milk, and Unpasteurized Whole Milk," *Applied and Environmental Microbiology*, vol. 66, No. 10, pp. 4266-4271, Oct. 2000.

Paillard, et al. "Rapid Identification of Listeria Species by Using Restriction Fragment Length Polymorphism of PCR-Amplified 23S rRNA Gene Fragments," *Applied and Environmental Microbiology*, vol. 69, No. 11, pp. 6386-6392, Nov. 2003.

(Continued)

*Primary Examiner* — Teresa E Strzelecka
(74) *Attorney, Agent, or Firm* — Knobbe, Martens, Olson & Bear, LLP

(57) ABSTRACT

Live cells of a microorganism in a test sample are detected by the following steps:

a) the step of treating the test sample with a topoisomerase poison and/or a DNA gyrase poison, b) the step of extracting DNA from the test sample, and amplifying a target region of the extracted DNA by PCR, and c) the step of analyzing an amplification product.

13 Claims, 16 Drawing Sheets

(56) References Cited

OTHER PUBLICATIONS

Office Action issued Nov. 24, 2009 by the Korean Patent Office to corresponding Korean application No. 10-2008-7001379.

Nogva, et al. "Ethidium Monoazide for DNA-Based Differentiation of Viable and Dead Bacteria by 5'-Nuclease PCR," *BioTechniques*, vol. 34, No. 4, pp. 804-813, Apr. 2003.

Rueckert, et al. "Rapid Differentiation and Enumeration of the Total, Viable Vegetative Cell and Spore Content of Thermophilic bacilli in Milk Powders with Reference to *Anoxybacillus flavithermus*," *Journal of Applied Microbiology*, vol. 99, No. 5, pp. 1246-1255, 2005.

Rudi, et al. "Quantification of Viable and Dead Cells in Complex Samples Using Ethidium-Monoazide Treated DNA and 5'-Nuclease PCR," *Abstracts of the General Meeting of the American Society for Microbiology*, vol. 105, p. 330, 2005.

Rudi, et al. "Development and Application of New Nucleic Acid-Based Technologies for Microbial Community Analyses in Foods," *International Journal of Food Microbiology*, vol. 78, pp. 171-180, 2002.

Nocker, et al. "Selective Removal of DNA from Dead Cells of Mixed Bacterial Communities by Use of Ethidium Monoazide," *Applied and Environmental Microbiology*, vol. 72, No. 3, pp. 1997-2004, Mar. 2006.

Database EMBL [Online], "Sequence 3 from Patent WO2005049206," retrieved from EBI accession No. EMBL:CS104686, Jun. 10, 2005.

Database Geneseq [Online], "*Listeria monocytogenes* 3' primer for analyte detection," retrieved from EBI accession No. GSN:AEA25750, Aug. 11, 2005.

Riedy, et al. "Use of a Photolabeling Technique to Identify Nonviable Cells in Fixed Homologous or Heterologous Cell Populations," *Cytometry*, vol. 12, No. 2, pp. 133-139, 1991.

Froelich-Ammon, et al. "Topoisomerase Poisons: Harnessing the Dark Side of Enzyme Mechanism," *Journal of Biological Chemistry*, vol. 270, No. 37, pp. 21429-21432, Sep. 15, 1995.

Supplementary European Search Report Aug. 24, 2009.

Luo et al., "Method to detect only viable cells in microbial ecology," Appl Microbiol Biotechnol, vol. 86, pp. 377-384 (2010).

\* cited by examiner

SEQUENCE LISTING

```
<160> NUMBER OF SEQ ID NOS: 8

<210> SEQ ID NO 1
<211> LENGTH: 25
<212> TYPE: DNA
<213> ORGANISM: Artificial
<220> FEATURE:
<223> OTHER INFORMATION: primer 23S-F

<400> SEQUENCE: 1
cagtcagagg cgatgaagga cgtgc                                        25

<210> SEQ ID NO 2
<211> LENGTH: 25
<212> TYPE: DNA
<213> ORGANISM: Artificial
<220> FEATURE:
<223> OTHER INFORMATION: primer 23S-R

<400> SEQUENCE: 2
ccggttagct caacccatcg ctgcg                                        25
```

<210> SEQ ID NO 3
<211> LENGTH: 21
<212> TYPE: DNA
<213> ORGANISM: Artificial
<220> FEATURE:
<223> OTHER INFORMATION: primer 23S-MF

<400> SEQUENCE: 3
accaggattt tggcttagaa g                                                  21

<210> SEQ ID NO 4
<211> LENGTH: 20
<212> TYPE: DNA
<213> ORGANISM: Artificial
<220> FEATURE:
<223> OTHER INFORMATION: primer 23S-MR

<400> SEQUENCE: 4
cacttacccc gacaaggaat                                                    20

<210> SEQ ID NO 5
<211> LENGTH: 16
<212> TYPE: DNA
<213> ORGANISM: Artificial
<220> FEATURE:
<223> OTHER INFORMATION: primer 16S-F

<400> SEQUENCE: 5
agtttgatcc tggctc                                                        16

<210> SEQ ID NO 6
<211> LENGTH: 16
<212> TYPE: DNA
<213> ORGANISM: Artificial
<220> FEATURE:
<223> OTHER INFORMATION: primer 16S-R

<400> SEQUENCE: 6
ggctaccttg ttacga                                                        16

<210> SEQ ID NO 7
<211> LENGTH: 19
<212> TYPE: DNA
<213> ORGANISM: Artificial
<220> FEATURE:
<223> OTHER INFORMATION: primer hlyA-F

<400> SEQUENCE: 7
tgcaagtcct aagacgcca                                                     19

<210> SEQ ID NO 8
<211> LENGTH: 24
<212> TYPE: DNA
<213> ORGANISM: Artificial
<220> FEATURE:
<223> OTHER INFORMATION: primer hlyA-R

<400> SEQUENCE: 8 cactgcatctccgtggtatactaa                                                 24

METHOD FOR DETECTION OF MICROORGANISM AND KIT FOR DETECTION OF MICROORGANISM

CROSS-REFERENCE TO RELATED APPLICATIONS

This application is the U.S. National Phase under 35 U.S.C. §371 of International Application PCT/JP2006/302893, filed Feb. 17, 2006, which was published in a non-English language.

TECHNICAL FIELD

The present invention relates to a method for detecting a microorganism contained in foodstuffs or clinical samples, and a kit for detecting a microorganism. More precisely, the present invention relates to a method and kit for detection of a microorganism that enable selective detection of live cells of a microorganism contained in foodstuffs or clinical samples.

BACKGROUND ART

The plate culture method has been conventionally used for measurement of general live bacterial counts in foodstuffs, clinical samples or environments. However, the plate culture method requires time of about two days to obtain a result.

Because of the improvements of sterilization techniques and processing techniques for foodstuffs, needs for distinguishing live and dead states of microorganisms existing in test samples are increasing even for the cases where the cells exist in an extremely small amount. In the fields of food sanitation inspection and clinical test, in particular, as a quick method for detecting bacteria, it is attempted to determine presence or absence of bacteria and quantify bacteria by amplifying genes specific to the bacteria by PCR to such an amount that the genes can be visually observed. However, if a bacterial DNA is targeted, the background originated from dead cells originally contained in the test sample is also detected, and therefore a positive result obtained by PCR does not necessarily suggest the presence of live bacteria. Therefore, the current situation in the fields of food sanitation and clinical test is that PCR is not used widely, although it is a highly sensitive and quick technique.

In these days, it is attempted to detect and quantify only live cells in a test sample by preparing cDNA with reverse transcriptase for mRNA as a target and performing PCR with primers specific to various bacteria. However, in this method, the reverse transcription of mRNA of dead cells itself is not inhibited, and when $10^4$ cfu/ml or $10^4$ cfu/g or more of dead cells are contained in the test sample, background originated from the dead cells is detected. Therefore, this method cannot be said to be sufficient as a method for distinguishing the live and dead states.

Specifically, as a method for distinguishing live and dead states of microorganisms such as bacteria using the PCR method, the methods described in Patent document 1 and 2 have been disclosed. However, the following problems remain in these methods for distinguishing live and dead states of microorganisms such as bacteria using the PCR method.

As for the technique disclosed in Patent document 1, examples are mentioned for distinction of dead cells contained in boiled foodstuffs subjected to high temperature long time sterilization at 100° C. for 10 to 30 minutes, and distinction of microorganisms contained in foodstuffs subjected to ethanol sterilization or formaldehyde sterilization. However, there are not foodstuffs actually subjected to such pasteurization treatments, especially the treatment of the latter type. Moreover, there are not supposed detection of only live microorganisms subjected to the currently major pasteurization method in the food industry, low temperature long time pasteurization (LTLT pasteurization), high temperature short time pasteurization (HTST pasteurization), or ultra high temperature pasteurization (UHT pasteurization), and detection of only live specific pathogenic bacteria in clinical specimens of infectious disease patients administered with antibiotics. Moreover, in the case of a test sample of a foodstuff or clinical specimen containing dead cell background at a concentration of $10^4$ cfu/ml or higher, the amounts of the final PCR amplification products derived from dead cells exceed the detection limit of the technique of Patent document 1, and therefore it is impossible to determine whether a positive response of a test sample obtained by PCR is derived from live cells or dead cells.

Further, as the technique of Patent document 2, disclosed is a method of distinguishing live cells and dead cells by utilizing relative decrease in RNA/DNA molar ratio of dead cells compared with that of live cells. In this method, the total RNA is extracted, complementary DNA is prepared by using a reverse transcription reaction, then PCR is performed to calculate the Ct value thereof, and the molar concentration of RNA is obtained by using a separately prepared calibration curve. Separately, a region of chromosomal DNA corresponding to that RNA is amplified by PCR to obtain the Ct value thereof, and the molar concentration of the chromosomal DNA is calculated on the basis of the calibration curve to obtain the RNA/DNA molar ratio. That is, the above procedure requires to perform troublesome extraction of total RNA and uses two steps of reverse transcription reaction and PCR. Therefore, this technique is inferior to usual PCR targeting DNA in quantification performance and quickness. Further, RNA is continuously produced in live cells, whereas RNA derived from dead cells is decomposed at an early stage. Therefore, the technique lacks stability. Furthermore, in a foodstuff or clinical specimen containing dead cells at a high concentration, only live cells of $\frac{1}{10}$ of that concentration can be detected by this technique. Therefore, it is difficult to apply this technique in the fields of food sanitation inspection and clinical test, which require quickness, high sensitivity and accuracy.

Patent document 1: International Patent Application Unexamined Publication in Japan No. 2000-530118

Patent document 2: International Patent Publication WO2002/052034 pamphlet

DISCLOSURE OF THE INVENTION

Problems to be Solved by the Invention

An object of the present invention is to provide a method for selectively detecting live cells (Viable-and-Culturable cells) of a microorganism contained in a foodstuff or clinical sample in contrast to dead cells or injured cells (Injured cells or Viable-but-Non-Culturable cells (VNC cells)), that is, a quick detection method alternative to the culture method, but succeeding the characteristics of the culture method as they are, and a kit for performing the method.

Means for Solving the Problem

The inventors of the present invention assiduously researched on a method for determining cells to be alive or dead applicable to various sterilization methods, showing high detection sensitivity, suitable for food sanitation inspection, and also enabling detection of specific pathogenic bacteria in infectious disease patients at hospitals or clinical sites. As a result, they found that, in a method for distinguishing live cells and injured cells of a microorganism in a test sample, by treating the test sample with a topoisomerase poison and/or a DNA gyrase poison, or by treating the test sample with ethidium monoazide, irradiation with visible light, and a topoisomerase poison and/or DNA gyrase poison other than ethidium monoazide, chromosomal DNA of live cells could be selectively amplified by PCR, and a quick method alternative to the culture method could be provided. Thus, they accomplished the present invention.

That is, the present invention provides a method for detecting live cells of a microorganism in a test sample, which comprises the following steps:
a) the step of treating the test sample with a topoisomerase poison and/or a DNA gyrase poison,
b) the step of extracting DNA from the test sample, and amplifying a target region of the extracted DNA by PCR, and
c) the step of analyzing an amplification product.

In a preferred embodiment of the aforementioned method, the amplification product is analyzed by using a standard curve representing relationship of amount of the microorganism and the amplification product, which prepared by using standard samples of the microorganism.

In a preferred embodiment of the aforementioned method, PCR is performed by real-time PCR, and PCR and analysis of the amplification product are simultaneously performed.

In a preferred embodiment of the aforementioned method, the test sample is one of milk, a dairy product, a foodstuff produced from milk or a dairy product as a raw material, a blood sample, a urine sample, a spinal fluid sample, a synovial fluid sample and a pleural fluid sample.

In a preferred embodiment of the aforementioned method, the microorganism is a bacterium.

In a preferred embodiment of the aforementioned method, the target region is the 23S rRNA gene. In this embodiment, PCR is preferably performed by using a primer set of the primers of SEQ ID NOS: 1 and 2, or a primer set of the primers of SEQ ID NOS: 3 and 4.

In a preferred embodiment of the aforementioned method, the microorganism is a pathogenic bacterium. In this embodiment, the target region is preferably a pathogenic gene. Further, in this embodiment, PCR is preferably performed by using a primer set of the primers of SEQ ID NOS: 7 and 8.

In a preferred embodiment of the aforementioned method, the topoisomerase poison is selected from amsacrine, camptothecin, doxorubicin, ellipticine, etoposide, mitoxantrone, saintopin, topotecan and CP-115,953.

In a preferred embodiment of the aforementioned method, the DNA gyrase poison is selected from ciprofloxacin, ofloxacin, enoxacin, pefloxacin, fleroxacin, norfloxacin, nalidixic acid, oxolinic acid and piromidic acid.

In a preferred embodiment of the aforementioned method, the topoisomerase poison and/or the DNA gyrase poison is ethidium monoazide, and the method comprises the step of subjecting the test sample to which ethidium monoazide is added to irradiation of visible light.

In a preferred embodiment of the aforementioned method, the test sample is treated with ethidium monoazide, and a topoisomerase poison and/or DNA gyrase poison other than ethidium monoazide.

In a preferred embodiment of the aforementioned method, the following step is performed before the aforementioned step a):

d) the step of treating the test sample with a topoisomerase and/or a DNA gyrase.

Further, the aforementioned method provides a kit for detecting live cells of a microorganism in a test sample by PCR, which comprises the following elements:
a topoisomerase poison and/or a DNA gyrase poison, and primers for amplifying a target region of DNA of a microorganism to be detected by PCR.

In a preferred embodiment of the aforementioned kit, the kit comprises a topoisomerase and/or a DNA gyrase.

In a preferred embodiment of the aforementioned kit, the topoisomerase poison is selected from amsacrine, camptothecin, doxorubicin, ellipticine, etoposide, mitoxantrone, saintopin, topotecan and CP-115,953.

In a preferred embodiment of the aforementioned kit, the DNA gyrase poison is selected from ciprofloxacin, ofloxacin, enoxacin, pefloxacin, fleroxacin, norfloxacin, nalidixic acid, oxolinic acid and piromidic acid.

In a preferred embodiment of the aforementioned kit, the kit comprises ethidium monoazide, and a topoisomerase poison and/or DNA gyrase poison other than ethidium monoazide.

In a preferred embodiment of the aforementioned kit, the aforementioned primers consist of a primer set of the primers of SEQ ID NOS: 1 and 2, or a primer set of the primers of SEQ ID NOS: 3 and 4.

In another preferred embodiment of the aforementioned kit, the aforementioned primers consist of a primer set of the primers of SEQ ID NOS: 7 and 8.

BEST MODE FOR CARRYING OUT THE INVENTION

Figure 1:
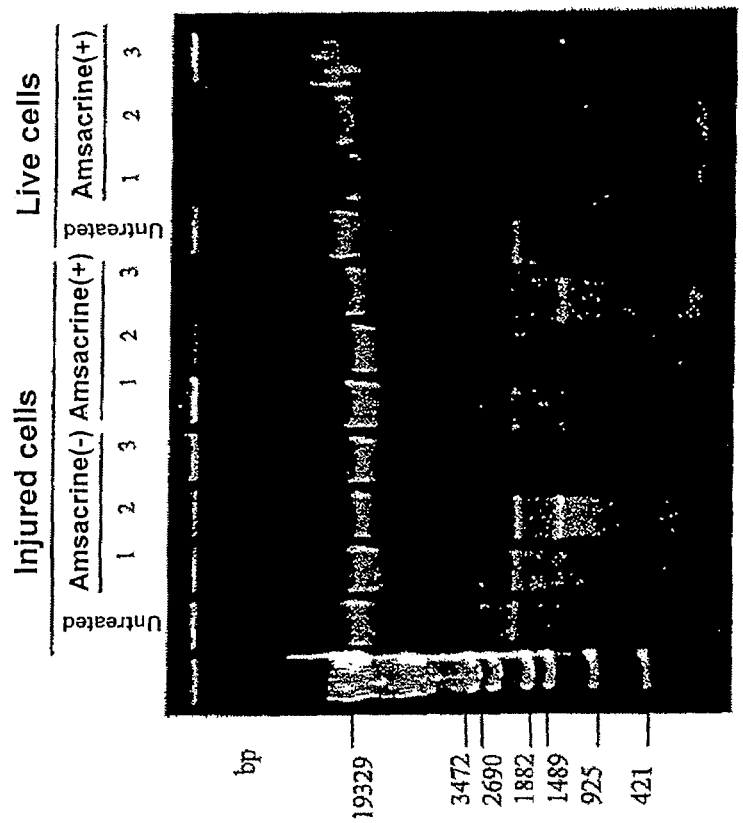
FIG. 1 Electrophoresis photographs showing influence of injured cell intracellular DNase on chromosomal DNA of *Listeria* (injured cells), influence of amsacrine on chromosomal DNA of *Listeria* (injured cells), and influence of amsacrine on chromosomal DNA of *Listeria* (live cells):
Non: Untreated,
Amsacrine(−): No addition of amsacrine,
Amsacrine(+): Addition of amsacrine,
1: Incubation at 30° C. for 24 hours,
2: Incubation at 30° C. for 48 hours,
3: Incubation at 30° C. for 72 hours.

Hereafter, preferred embodiments of the present invention will be explained in detail. However, the present invention is not limited to the following preferred embodiments, and can be freely modified within the scope of the present invention. In this specification, percentages are used on mass basis unless especially indicated.

<1> Method of the Present Invention

The method of the present invention is a method for detecting live cells of a microorganism in a test sample, which comprises the following steps:
a) the step of treating the test sample with a topoisomerase poison and/or a DNA gyrase poison,
b) the step of extracting DNA from the test sample, and amplifying a target region of the extracted DNA by PCR, and
c) the step of analyzing an amplification product.

In this specification, the "test sample" is an object for which live cells of a microorganism existing therein are detected, and it is not particularly limited so long as the presence of live cells can be detected by amplification of a specific region of chromosomal DNA by PCR. Examples include foodstuffs, for example, milk, dairy products, foodstuffs using milk or a dairy product as a raw material, blood samples, urine samples, spinal fluid samples, synovial fluid samples, pleural fluid samples, and so forth. Milk, dairy products, foodstuffs using milk or a dairy product as a raw material are especially preferred. In the present invention, the test sample may be any one of the aforementioned products and biosamples themselves, and may be one obtained by diluting or concentrating any one of the aforementioned products and biosamples or subjecting any one of the aforementioned products and biosamples to a pretreatment other than the treatment according to the method of the present invention. Examples of the pretreatment include heat treatment, filtration, centrifugation, and so forth.

The "microorganism" is an object to be detected by the method of the present invention, and is not particularly limited so long as it can be detected by PCR, and a topoisomerase poison and a DNA gyrase poison act on live cells of the microorganism in a manner different from that for dead cells and injured cells of the microorganism. Preferred examples include bacteria, filamentous fungi, yeasts, and so forth. The bacteria include both gram-positive bacteria and gram-negative bacteria. Examples of the gram-positive bacteria include *Staphylococcus* bacteria such as *Staphylococcus epidermidis*, *Streptococcus* bacteria, *Listeria* bacteria such as *Listeria monocytogenes*, *Bacillus* bacteria such as *Bacillus cereus*,

*Mycobacterium* bacteria, and so forth. Examples of the gram-negative bacteria include enteric bacteria typified by *Escherichia* bacteria such as *Escherichia coli, Enterobacter* bacteria such as *Enterobacter sakazakii, Citrobacter* bacteria such as *Citrobacter koseri*, and *Klebsiella* bacteria such as *Klebsiella oxytoca*, and *Salmonella* bacteria, *Vibrio* bacteria, *Pseudomonas* bacteria, and so forth.

In the present invention, the "live cell" refers to a cell in a state that the cell can proliferate, and exhibits metabolic activities of the microorganism (Viable-and-Culturable state), when it is cultured under a generally preferred culture condition, and is a cell substantially free from injury of cell wall. As the metabolic activities mentioned above, ATP activity, esterase activity etc. can be exemplified.

The "dead cell" is a cell in a state that it cannot proliferate, and does not exhibit metabolic activities (dead state), even if it is cultured under an optimum culture condition. Moreover, it is in a state that although structure of cell wall is maintained, the cell wall itself is highly injured, and a nuclear stain agent exhibiting weak permeability such as propidium iodide can penetrate the cell wall.

The "injured cell" (injured cell or Viable-but-non Culturable cell) is a cell in a state that it hardly proliferates even when it is cultured under an optimum culture condition, because it is injured due to artificial stress or environmental stress, and it shows metabolic activities at a lower level compared with a live cell, but a significant level compared with a dead cell.

Detection of bacteria exhibiting the state of injured cell by using mild heat treatment or administration of antibiotics is attracting attention particularly in the field of food sanitation inspection and clinical test, and the present invention provides a method for detecting a microorganism, which enables not only detection of live cells, but also distinction of live cells from dead cells or injured cells.

The unit of cell number of live cells, injured cells and dead cells is usually represented by cell number (cells)/ml. The number of live cells can be approximated with a number of colonies (cfu/ml (colony forming units/ml)) formed by culturing the cells under an optimum condition on a suitable plate medium. A standard sample of injured cells can be prepared by subjecting a live cell suspension to a heat treatment, for example, a heat treatment in boiling water. In this case, the number of injured cells in such a sample can be approximated with cfu/ml of the live cell suspension before the heat treatment. Although time of the heat treatment in boiling water for preparing injured cells varies depending on type of microorganism, injured cells of the bacteria described in the examples, for example, can be prepared by a heat treatment of about 50 seconds. Further, a standard sample of injured cells can also be prepared by a treatment with an antibiotic. In such a case, the cell number of injured cells can be approximated with the number of colonies (cfu/ml) formed when the cells are cultured under an optimum condition on a suitable plate medium, by removing the antibiotic after treating live cell suspension with the antibiotic, measuring transmittance of visible light (wavelength: 600 nm), that is turbidity, and comparing the turbidity with that of a live cell suspension which density of live cell is known.

The method of the present invention is for detection of live cells, and cells of the microorganism distinguished from live cells may be injured cells or dead cells.

In the present invention, the "detection of live cells" includes both determination of presence or absence of live cells in a test sample and determination of amount of live cells in a test sample. The amount of live cells is not limited to an absolute amount, and may be a relative amount with respect to that in a control sample.

Hereafter, the method of the present invention will be explained for every step.

(1) Step a)

The test sample is treated with a topoisomerase poison and/or a DNA gyrase poison.

The topoisomerase poison and the DNA gyrase poison used for the present invention refer to those not inhibiting the activities of topoisomerase and DNA gyrase for cleaving DNAs, respectively, but inhibiting religation of DNAs, or enhancing forward rate of DNA cleavage. The topoisomerase poison and the DNA gyrase poison are preferably those that bind to chromosomal DNAs of a microorganism by covalent attachment, those that intercalate into the chromosomal DNAs and bind to chromosomal DNAs by covalent attachment upon irradiation of visible light, those that simply intercalate into the chromosomal DNAs, or those that form a complex with topoisomerase or DNA gyrase.

Both the topoisomerase poison and DNA gyrase poison may be used, or either one may be used.

The topoisomerase poison and the DNA gyrase poison are preferably those exhibiting different actions on live cells, and injured cells, dead cells, somatic cells such as bovine leucocytes, leucocytes and thrombocytes etc., more specifically, those exhibiting higher permeability for cell walls of injured cells and dead cells and cell membranes of somatic cells such as bovine leucocytes, leucocytes and thrombocytes etc., compared with that for cell walls of live cells.

Examples of the topoisomerase poison include amsacrine, camptothecin, doxorubicin, ellipticine, etoposide, mitoxantrone, saintopin, topotecan, CP-115,953, and so forth. One kind of topoisomerase poison may be independently used, or two or more kinds of them may used in combination.

Examples of the DNA gyrase poison include ciprofloxacin, ofloxacin, enoxacin, pefloxacin, fleroxacin, norfloxacin, nalidixic acid, oxolinic acid, piromidic acid, and so forth. One kind of DNA gyrase poison may be independently used, or two or more kinds of them may used in combination.

The conditions for the treatment with the topoisomerase poison or DNA gyrase poison may be suitably determined. For example, conditions that enables easy distinction of live cells from dead cells and injured cells can be determined by adding a topoisomerase poison or DNA gyrase poison at various concentrations to suspensions of live cells and dead cells or injured cells of the microorganism as an object of detection, leaving them for various periods of time, then harvesting the cells by centrifugation or the like, and analyzing the cells by PCR. Furthermore, conditions that enables easy distinction of live cells of the microorganism as an object of detection from somatic cells such as bovine leucocytes, thrombocytes and the like can be determined by adding a topoisomerase poison at various concentrations to suspensions of the live cells and the aforementioned various cells, leaving them for a predetermined time, then harvesting the live cells and the aforementioned various cells by centrifugation or the like, and analyzing the cells by PCR. Examples of such conditions include, specifically, a final concentration of 1 to 100 μg/ml, temperature of 25 to 37° C., and treatment time of 5 minutes to 48 hours for amsacrine, a final concentration of 0.05 to 5 μg/ml, temperature of 25 to 37° C., and treatment time of 10 minutes to 48 hours for ellipticine, a final concentration of 1 to 100 μg/ml, temperature of 25 to 37° C., and treatment time of 10 minutes to 48 hours for camptothecin, a final concentration of 0.4 to 40 μg/ml, temperature of 25 to 37° C., and treatment time of 10 minutes to 48 hours for ciprofloxacin, a final concentration of 1 to 100 μg/ml, temperature of 25 to 37° C., and treatment time of 5 minutes to 48 hours for etoposide, and a final concentration of 0.1 to 10 μg/ml, temperature of 25 to 37° C., and treatment time of 10 minutes to 48 hours for mitoxantrone. After the test sample is treated under the predetermined conditions, the treatment is preferably terminated by elimination by dilution, and/or centrifugal separation or the like.

The aforementioned topoisomerase poison and DNA gyrase poison are more likely to penetrate cell walls of injured cells and dead cells compared with cell walls of live cells. Therefore, it is considered that if the treatment time is within the ranges mentioned above, the poisons do not substantially penetrated cell walls of live cells, but they penetrate cell walls of injured cells, dead cells and live somatic cells as dead cells. It is also considered that they penetrate into even live somatic cells, since they have only cell membranes, but no cell walls. It is estimated that the topoisomerase poison or DNA gyrase poison penetrates into dead cells of somatic cells, dead bacteria and injured bacteria as a result, then disorderly bind to chromosomal DNAs by covalent attachment, intercalates into the DNAs, or forms a complex with the topoisomerase, and further inhibits religation of the DNAs by topoisomerase II or topoisomerase I in somatic cells, or topoisomerase IV, or topoisomerases I, III or DNA gyrase in dead cells or injured cells, or enhances the forward rate of DNA cleavage to cause fragmentation of the chromosomal DNAs.

If the chromosomal DNAs of injured cells and dead cells are preferentially fragmented compared with those of live cells, a target region of chromosomal DNA is amplified by PCR in live cells, whereas cleavage of the target region in injured cells or dead cells inhibits PCR amplification. With amsacrine or camptothecin, for example, crosslinking is further caused, and thus PCR amplification is inhibited. Therefore, live cells can be more selectively detected by PCR compared with injured cells or dead cells.

In dead cells, activity of intracellular topoisomerase and/or DNA gyrase may be lost. Moreover, the activities of these enzymes may also be decreased or lost in injured cells. Therefore, in a preferred embodiment of the present invention, the test sample is treated with a topoisomerase and/or a DNA gyrase prior to the step a) (step d)). The step d) will be explained later in detail.

In another preferred embodiment of the present invention, the topoisomerase poison or the DNA gyrase poison is ethidium monoazide, and the method comprises the step of subjecting the test sample, to which ethidium monoazide is added, to irradiation of visible light. Ethidium monoazide (EMA) is more likely to penetrate cell walls of injured cells or dead cells compared with cell walls of live cells of microorganisms. Therefore, it is considered that EMA does not substantially penetrate cell walls of live bacteria, but it penetrates cell walls of injured bacteria and dead bacteria, and cell membranes of somatic cells as dead cells. When leucocytes and thrombocytes in blood are live cells, EMA becomes more likely to penetrate cell membranes of the cells in sterilized water or a hypotonic salt solution. EMA penetrates into somatic cells as dead cells, injured bacteria, and dead bacteria, and disorderly intercalates into chromosomal DNAs, and then only intercalating EMA is converted into nitrene by irradiation of visible light, and binds to the chromosomal DNAs by covalent attachment. It is estimated that then it inhibits religation of the DNAs by topoisomerase II in somatic cells, topoisomerase IV or DNA gyrase in injured bacteria or dead bacteria, to cause fragmentation of the chromosomal DNAs.

Conditions for the treatment with EMA can be appropriately determined. For example, conditions that enables easy distinction of live cells from injured cells can be determined by adding EMA at various concentrations to suspensions of live cells, injured cells and dead cells of the microorganism as an object of detection, leaving them for various periods of time, then irradiating them with visible light, harvesting the cells by centrifugation or the like as required, and analyzing the cells by PCR.

Preferred conditions for the irradiation of visible light can also be appropriately determined by performing such an experiment as mentioned above using various irradiation times. Specifically, the treatment with EMA is preferably performed with a final concentration of 0.5 to 100 μg/ml at a temperature of 4 to 10° C. for 5 minutes to 48 hours. Moreover, the EMA treatment is preferably performed under light shielding. As the visible light, visible lights containing 500 to 700 nm components are preferred. Specific examples of the conditions for the irradiation of visible light include irradiation of visible lights of 100 to 750 W for 5 minutes to 2 hours from a distance of 10 to 50 cm from the test sample. The irradiation of visible light is preferably performed at a low temperature, for example, with ice cooling of the sample.

In a particularly preferred embodiment of the present invention, the test sample is subjected to the EMA treatment, irradiation of visible light, and treatment with a topoisomerase poison and/or DNA gyrase poison other than EMA. In such a case, the order of the EMA treatment, irradiation of visible light, and treatment with a topoisomerase poison and/or DNA gyrase poison other than EMA is not particularly limited, and these treatments may be simultaneously performed.

(2) Step b)

DNA is extracted from the test sample treated in the step a), and a target region of the extracted DNA is amplified by PCR (White, T. J. et al., Trends Genet., 5, 185 (1989)).

The method for extracting DNA from the test sample is not particularly limited so long as the extracted DNA can function as a template in PCR, and the extraction can be attained according to a commonly used method for extracting DNA of a microorganism.

The DNA extraction method is described in, for example, Maniatis T., Fritsch E. F., Sambrook, J., "Molecular Cloning: A Laboratory Manual", 3rd edn., Cold Spring Harbor, N.Y.: Cold Spring Harbor Laboratory Press, 2001.

In the present invention, the "target region" is not particularly limited so long as a region of a chromosomal DNA that can be amplified by PCR using primers used for the present invention and enables detection of a microorganism to be detected is chosen, and it can be suitably chosen depending on the purpose. For example, when cells of a type different from that of the microorganism to be detected are contained in the test sample, the target region preferably contains a sequence specific to the microorganism as an object of the detection. Further, depending on the purpose, the target region may be one containing a sequence common to several kinds of microorganisms. Furthermore, the target region may consist of a single region or two or more regions. If a primer set suitable for a target region specific to the microorganism as an object of the detection and a primer set suitable for chromosomal DNAs of wide varieties of microorganisms are used, live cell amount of the microorganism as the object of the detection and live cell amount of the wide varieties of microorganisms can be simultaneously measured. Length of the target region is, for example, usually 80 to 3000 nucleotides, preferably 900 to 3000 nucleotides, particularly preferably 2000 to 3000 nucleotides. Specific examples include the 16S rRNA gene and the 23S rRNA gene. Among these, the 23S rRNA gene is preferred.

Primers used for PCR are not particularly limited, so long as those enabling specific amplification of the aforementioned target region are chosen. Specific examples of primers suitable for the 23S rRNA gene include the primer set of the primers shown as SEQ ID NOS: 1 and 2, and the primer set of the primers shown as SEQ ID NOS: 3 and 4. Examples of primers suitable for the 16S rRNA gene include the primer set of the primers shown as SEQ ID NOS: 5 and 6.

When the microorganism as the object of the detection is a pathogenic bacterium, examples of the target region include a pathogenic gene. Examples of the pathogenic gene include the listeriolysin O (hlyA) gene of Listeria bacteria, enterotoxin gene and invA gene of Salmonella bacteria, verotoxin gene of pathogenic E. coli O-157, MMS gene of Enterobacter bacteria (Enterobacter sakazakii), Staphylococcus aureus enterotoxin gene, cereulide (emetic toxin) gene and enterotoxin gene of Bacillus cereus, the various toxin genes of Clostridium botulinum, and so forth. Examples of primers suitable for the pathogenic gene include the primer set of the primers of SEQ ID NOS: 7 and 8.

If primers suitable for two or more kinds of microorganisms are used, live cells of two or more kinds of the microorganisms in a test sample can be detected. Moreover, if primers specific to a particular bacterium are used, live cell of the particular bacterium in a test sample can be detected.

Conditions of PCR are not particularly limited so long as the specific amplification is attained in accordance with the principle of PCR, and they can be suitably determined.

In the embodiment where the EMA treatment and the visible light treatment are performed among the embodiments of the present invention, if the target region is long, for example, it consists of 2000 or more nucleotides, live cells can be effectively detected even only with the EMA treatment and the visible light irradiation treatment. In contrast, when the target region is short, for example, it consists of 200 or less of nucleotides, it is preferable to use the treatment with a topoisomerase poison and/or DNA gyrase poison other than EMA in combination with the EMA treatment and the visible light treatment.

(3) Step c)

Then, the PCR amplification product is analyzed. Analysis method is not particularly limited, so long as a method enabling detection or quantification of the PCR amplification product is chosen, and examples include electrophoresis, real-time PCR (Nogva et al., Application of 5'-nuclease PCR for quantitative detection of Listeria monocytogenes in pure cultures and water, skim milk and unpasteurized whole milk, Appl. Environ. Microbiol., vol. 66, 2000, pp. 4266-4271; Nogva et al., Application of the 5'-nuclease PCR assay in evaluation and development of methods for quantitative detection of Campylobacter jejuni, Appl. Environ. Microbiol., vol. 66, 2000, pp. 4029-4036), and so forth. By electrophoresis, amount and size of the PCR amplification product can be evaluated. By real-time PCR, the PCR amplification product can be quickly quantified. When the real-time PCR is employed, since changes of fluorescence intensity generally corresponds to the noise level, and substantially equal to zero for amplification cycle numbers of 1 to 10, these changes can be considered values for sample blank containing no amplification product. A fluorescence intensity value obtained by calculating the standard deviation SD of the changes in fluorescence intensity for amplification cycle numbers of 1 to 10, and multiplying the standard deviation by 10 is defined as a threshold value. The PCR cycle number of the cycle first providing a fluorescence intensity change exceeding the threshold value is called a cycle threshold value (Ct value). Therefore, a larger initial amount of a DNA template in a PCR solution provides a smaller Ct value, whereas a smaller initial amount of a DNA template in a PCR solution provides a larger Ct value. Further, even with the same amount of a DNA template, a larger occurrence rate of cleavage of a PCR target region in a template provides a larger Ct value for PCR of that region.

Further, presence or absence of the amplification product can also be determined by analyzing the melting temperature (TM) pattern of the amplification product.

All the aforementioned methods can also be used for optimization of various conditions for the method of the present invention.

When live cells are detected by the method of the present invention, precisions of the determination of the presence or absence of live cells and quantification of the same in the analysis of the PCR amplification product can be increased by using a standard curve representing relationship between the amount of microorganism and the amplification product and prepared by using standard samples of the identified microorganism. Although a preliminarily prepared standard curve may be used, it is preferable to use a standard curve prepared by simultaneously performing the steps of the method of the present invention for standard samples and a test sample. Moreover, if relationship between amount of microorganism and amount of DNA is determined beforehand, DNA isolated from the microorganism can also be used as a standard sample.

(4) Step d)

As described above, intracellular activity of topoisomerase and/or DNA gyrase may be lost in dead cells, and even after a treatment with a topoisomerase poison or a DNA gyrase poison, chromosomal DNA may not be cleaved. Even in such a case, if the test sample is treated with a topoisomerase and/or a DNA gyrase before the step a), DNA cleavage selective to DNA in dead cells occurs, and therefore amplification of the target region by PCR can be inhibited.

Both the topoisomerase and the DNA gyrase may be used, or either one of them may be used. Moreover, for each enzyme, one kind of enzyme may be used, or two or more kinds of enzymes may be used together.

Specific examples of the conditions for the reaction by the topoisomerase or DNA gyrase include the conditions mentioned in the reference examples mentioned later. However, in general, a supernatant containing microorganisms collected from a foodstuff or clinical specimen such as blood is subjected to refrigerated centrifugation at 4° C. and 14,000×g for 10 minutes, the supernatant is removed, 1 mL of a buffer for DNA cleavage (10 mM Tris-HCl buffer, pH 7.9, 50 mM potassium chloride, 50 mM sodium chloride, 5 mM magnesium chloride, 0.01 mM EDTA, 2.5% glycerol) is added to the residue, a topoisomerase or DNA gyrase is added to the mixture at a final concentration of 1 to 50 mM, ATP is further added at a final concentration of 1 to 50 mM, and the reaction is allowed at 30 to 37° C. for 5 to 30 minutes. Because ATP is required for the activities of topoisomerase and DNA gyrase, ATP or an ATP synthesis system is preferably added when the test sample is treated with these enzymes.

<3> Kit of the Present Inventions

The kit of the present invention is a kit for detecting live cells of a microorganism in a test sample by PCR, and comprises a topoisomerase poison and/or a DNA gyrase poison, and primers for amplifying a target region of DNA of a microorganism as an object of detection by PCR.

In the aforementioned kit, the topoisomerase poison and the DNA gyrase poison are the same as those explained for the method of the present invention.

In a preferred embodiment of the kit of the present invention, the kit contains EMA and another topoisomerase poison and/or DNA gyrase poison other than EMA as the topoisomerase poison and/or the DNA gyrase poison.

Moreover, the kit of the present invention comprises a topoisomerase and/or a DNA gyrase in addition to the aforementioned elements.

The kit of the present invention may further comprise a diluent, a reaction solution for the reaction by the topoisomerase and/or DNA gyrase, an instruction describing the method of the present invention and so forth.

EXAMPLES

Hereafter, the present invention will be more specifically explained with reference to the following examples. However, the present invention is not limited to the following examples.

Example 1

Live cells and injured cells of a microorganism were treated with a topoisomerase poison, respectively, and cleavage degree of each chromosomal DNA was examined.
1. Preparation of Samples
1-1) Preparation of Live Cell and Injured Cell Suspensions Listeria monocytogenes (Listeria monocytogenes JCM 2873, henceforth also referred to as "Listeria"), which is a gram-positive bacterium, was cultured at 30° C. by using the BHI broth, 40 ml of the culture medium in which the cells were at the logarithmic phase was subjected to refrigerated centrifugation at 4° C. and 8,000×g for 15 minutes, and the supernatant was removed. 40 ml of physiological saline was added to the cells, and the mixture was sufficiently stirred, and subjected to similar refrigerated centrifugation, the supernatant was removed, and then 10 ml of physiological saline was added to the cells to prepare a live cell suspension. When live cell count of this live cell suspension was measured on a standard agar plate medium, it was found to be $1.2\times10^9$ cfu/ml.

Further, 1 ml of the aforementioned live cell suspension was put into a 1.5 ml microtube, and the tube was immersed in boiling water for 50 seconds, and rapidly cooled with ice water to prepare an injured cell suspension. It is considered that the cells contained in this suspension contained a small number of live cells and dead cells, but the cells substantially consisted of injured cells, and therefore the cells were described as "injured cells". In addition, the method of the present invention is originally a method for detecting live cell, and cells of the microorganism distinguished from live cells may be injured cells or dead cells. The same shall apply to the other bacteria mentioned below.
1-2) Topoisomerase Poison Treatment 1 ml of each of the live cell suspension and injured cell suspension of Listeria prepared above ($1.2\times10^9$ cfu/ml, respectively) was added to 9 ml of newly prepared BHI broth (cell count in the medium was $1.2\times10^8$ cfu/ml for both the live cells and injured cells), and 100 µl of a 5 mg/ml amsacrine solution in DMSO was added to the medium. The final concentration of amsacrine was 50 µg/ml, and the final concentration of DMSO was 1%. Then, the cells of each type were incubated at 30° C. for 24 hours, 48 hours or 72 hours.

As for the injured cells, in order to investigate influence of active DNase remaining in the injured cells on the chromosomal DNA of the injured cells, 1 ml of the injured cell suspension was added to 9 ml of newly prepared BHI broth, then 100 µl of DMSO was added to the medium instead of the aforementioned amsacrine solution (final concentration of DMSO: 1%), and the cells were incubated at 30° C. for 72 hours. The live cell suspension and injured cell suspension in a volume of 1 ml each were used as controls.
1-3) Extraction of DNA Each suspension was subjected to refrigerated centrifugation at 4° C. and 8,000×g for 15 minutes, and the supernatant was completely removed. To the pellet, 0.5 ml of 5 mM EDTA solution was added, and 20 µl of an achromopeptidase solution (Wako Pure Chemical Industries, catalog number: 014-09661) prepared beforehand at 5 mg/ml with 10 mM NaCl aqueous solution was added, and the mixture was left at 50° C. for 30 minutes. Then, to the mixture, 0.5 ml of 10 mM Tris-HCl buffer (pH 8.0) was added, 20 µl of 1250 U/ml proteinase K (Sigma, E.C. 3.4.21.64) was added, 400 µl of a SDS solution prepared beforehand at 10% (w/v) with sterilized water was added, and the reaction was allowed overnight at 50° C.

Each treated suspension was put into two 2 ml volume microtubes in a half volume each, 0.5 ml of 1 M Tris-HCl buffer (pH 8.0)/saturated phenol was added to the suspension, and the mixture was gently stirred for 15 minutes. Then, 0.5 ml of chloroform was added to the mixture, and the mixture was gently stirred for 5 minutes. The mixture was subjected to refrigerated centrifugation at 4° C. and 6,000×g for 10 minutes, the aqueous layer of the upper layer was transferred to a new 2 ml volume microtube, 70 µl of 3 M sodium acetate buffer (pH 5.2) and 1.21 ml of 99.5% cold ethanol were added to the mixture, and the mixture was gently stirred. The mixture was subjected to refrigerated centrifugation at 4° C. and 15,000×g for 10 minutes, the supernatant was removed, and then the residue was washed with 0.4 ml of 70% cold ethanol. 0.5 ml of TE buffer (10 mM Tris-HCl buffer, 1 mM EDTA-2Na) was added to the pellet, and the mixture was left overnight at 4° C. to dissolve DNAs.

5 µl of an RNase (Sigma, E.C. 3.1.27.5) solution prepared beforehand at 10 mg/ml with sterilized water was added to the aforementioned DNA solution, and the mixture was incubated at 37° C. for 1 hour. 0.25 ml of phenol/chloroform (1/1) solution was added to the mixture, and the mixture was gently stirred for 10 minutes, 0.25 ml of chloroform was further added to the mixture, and the mixture was gently stirred for 5 minutes. The mixture was subjected to refrigerated centrifugation at 4° C. and 6,000×g for 10 minutes, the aqueous layer of the upper layer was transferred to a new 2 ml volume microtube, 50 µl of 3 M sodium acetate aqueous solution and 1 ml of 99.5% cold ethanol were added to the mixture, and the mixture was gently stirred. The mixture was subjected to refrigerated centrifugation at 4° C. and 15,000×g for 10 minutes, the supernatant was removed, then the residue was washed with 0.4 ml of 70% cold ethanol, and the pellet was dried (the aforementioned procedure is also referred to as the "RNase treatment").

125 µl of TE buffer was added to the dried pellet, and the mixture was left overnight at 4° C. to dissolve DNAs and thereby obtain extracted DNAs. Absorbance values of the purified DNA solution was measured at 260 nm and 280 nm ($OD_{260}$, $OD_{280}$, $OD_{260}$ of 50 µg/ml DNA solution was 1.0, cell length: 1 cm), DNA concentration was calculated from $OD_{260}$, and purity of the purified DNA was estimated on the basis of $OD_{260}/OD_{280}$.
2. Test Results The chromosomal DNAs extracted in 1-3) were subjected to electrophoresis by using 0.8% agarose gel. After completion of the electrophoresis, the agarose gel was immersed in a 1 µg/ml ethidium bromide aqueous solution for 20 minutes, and then washed twice with ion-exchanged water, and cleavage degree of the chromosomal DNAs was observed by using a UV transilluminator (wavelength: 254 nm).

The aforementioned extracted DNAs were analyzed by electrophoresis. The results are shown in FIG. 1. FIG. 1 shows influence of DNase contained in the injured cells on chromosomal DNAs of *Listeria* (injured cells), and influence of amsacrine on chromosomal DNAs of *Listeria* (live cells and injured cells).

As a result, when amsacrine was not added to the injured cell suspension of *Listeria*, and the cells were incubated up to 72 hours, any significant difference could not be seen for the extremely long DNA fragment remained in the well and the long DNA fragment located around 19,329 bp, and thus the chromosomal DNAs of the *Listeria* injured cell were hardly cleaved by DNase of which activity remained in the injured cells. However, if amsacrine was added to the injured cells, and the cells were incubated up to 72 hours, especially the extremely long DNA fragment remained in the well clearly decreased, and thus it was suggested that a state that the chromosomal DNAs were cleaved everywhere was attained by amsacrine with the aid of active DNA gyrase or topoisomerase remaining in the injured cells of *Listeria*.

Further, when amsacrine was added to the live cell suspension of *Listeria*, and the cells were incubated up to 72 hours, the extremely long DNA fragment remained in the well and the long DNA fragment located around 19,329 bp temporarily decreased at 24 hours, and when the incubation was continued thereafter, both the DNA fragments increased in proportion to the incubation time. This result suggested that amsacrine penetrated cell walls of the live cells at 24 hours to attain the chromosomal DNA cleavage state with the aid of the DNA gyrase or topoisomerase in the live cells, and remaining live cells of *Listeria* only slightly or hardly affected by the action of amsacrine proliferated by the second incubation.

Moreover, amsacrine is a yellow coloring and highly hydrophobic substance. Therefore, after a short action time of 1 to 30 minutes, it hardly penetrated uninjured cell walls of highly hydrophilic live cells, and thus the pellet of live cells was white. However, since injured cells had injured cell walls and increased hydrophobicity, amsacrine penetrated the cell walls of injured cells, and thus the pellet of the injured cells showed yellow color. It was confirmed by this example that, for both live cells and injured cells, if amsacrine penetrated cell walls, it attained a state that chromosomal DNAs were cleaved everywhere with the aid of the intracellular DNA gyrase and/or topoisomerase. However, within a short action time, the chromosomes of injured cells would be mildly, but selectively cleaved in a random manner, and therefore if cells are additionally treated with a topoisomerase poison such as amsacrine for a short period of time (for example, additional treatment after a treatment with a topoisomerase poison such as EMA), it becomes possible to distinguish live cells from injured cells or dead cells with high sensitivity by using PCR.

Example 2

Analysis was performed by PCR targeting the 23S rRNA gene using chromosomal DNAs of live cells and injured cells of microorganisms treated with a DNA gyrase poison.
1. Preparation of Samples
1-1) Preparation of Live Cell and Injured Cell Suspensions

*Enterobacter sakazakii* (*Enterobacter sakazakii* ATCC 51329 strain, henceforth also referred to as "*Enterobacter*"), which is a gram-negative bacterium, was cultured at 37° C. by using the BHI broth, 40 ml of the culture medium in which the cells were at the logarithmic phase was subjected to refrigerated centrifugation at 4° C. and 8,000×g for 15 minutes, and the supernatant was removed. 40 ml of physiological saline was added to the cells, and the mixture was sufficiently stirred, and subjected to similar refrigerated centrifugation, the supernatant was removed, and then 10 ml of physiological saline was added to the cells to prepare a live cell suspension. When live cell count of this live cell suspension was measured on a standard agar plate medium, it was found to be $4.4 \times 10^8$ cfu/ml.

Further, 1 ml of the aforementioned live cell suspension was put into a 1.5 ml microtube, and the tube was immersed in boiling water for 50 seconds, and rapidly cooled with ice water to prepare an injured cell suspension.

Live cell suspension and injured cell suspension of *Listeria monocytogenes* JCM 2873 were prepared in the same manner as that of Example 1. Live cell count in the live cell suspension was $4.0 \times 10^8$ cfu/ml.
1-2) DNA-Gyrase Poison (Ciprofloxacin) Treatment 1 ml of each of the *Enterobacter* (live cell and injured cell) suspensions and *Listeria* (live cell and injured cell) suspensions was added to 9 ml of newly prepared BHI broth (live cell count and injured cell count of *Enterobacter* in the medium were $4.4 \times 10^7$ cfu/ml and $4.4 \times 10^7$ cfu/ml, respectively, and live cell count and injured cell count of *Listeria* in the medium were $4.0 \times 10^7$ cfu/ml and $4.0 \times 10^7$ cfu/ml, respectively), and 2 ml of a ciprofloxacin solution (130 µg/ml, dissolved with physiological saline) was added to the medium.

As for the injured cells, in order to investigate influence of active DNase remaining in the injured cells on the chromosomal DNA of the injured cells, 1 ml of each of the injured cell suspensions of *Enterobacter* and *Listeria* was added to 9 ml of newly prepared BHI broth, and then 2 ml of physiological saline was added instead of the aforementioned ciprofloxacin solution.

Then, suspensions in which *Enterobacter* (live cells and injured cells) was cultured at 37° C. for 1 hour and 30 minutes, 3 hours and 30 minutes, 5 hours, and 72 hours were prepared. Further, suspensions in which *Listeria* (live cells and injured cells) was cultured at 37° C. for 1 hour and 30 minutes, 3 hours and 30 minutes, 5 hours, and 72 hours were prepared. Furthermore, as controls of culture time of 0 hour, live cell and injured cell suspensions of *Enterobacter* and *Listeria* were used as ciprofloxacin non-added live cell suspensions and ciprofloxacin non-added injured cell suspensions.

Each suspension was subjected to refrigerated centrifugation at 4° C. and 8,000×g for 15 minutes, the supernatant was completely removed, and a pellet was collected. DNAs were extracted by the following methods for *Enterobacter* and *Listeria*.
1-3) DNA Extraction DNAs of *Enterobacter* were extracted by the following method.

To the pellet, 0.5 ml of 10 mM Tris-HCl buffer (pH 8.0) was added, and 10 µl of 1250 U/ml proteinase K (Sigma, EC. 3.4.21.64) was added, 200 µl of an SDS solution prepared beforehand at 10% (w/v) with sterilized water was added, and the reaction was allowed overnight at 50° C. 0.5 ml of 1 M Tris-HCl buffer (pH 8.0)/saturated phenol was added to the treated suspension, and the mixture was gently stirred for 15 minutes. Then, 0.5 ml of chloroform was added to the mixture, and the mixture was gently stirred for 5 minutes. The mixture was subjected to refrigerated centrifugation at 4° C. and 6,000×g for 10 minutes, the aqueous layer of the upper layer was transferred to a new 2 ml volume microtube, 70 μl of 3 M sodium acetate buffer (pH 5.2) and 1.29 ml of 99.5% cold ethanol were added to the mixture, and the mixture was gently stirred. The mixture was subjected to refrigerated centrifugation at 4° C. and 15,000×g for 10 minutes, the supernatant was removed, and then the residue was washed with 0.4 ml of 70% cold ethanol. 0.5 ml of TE buffer (10 mM Tris-HCl buffer, 1 mM EDTA.2Na) was added to the pellet, and the mixture was left overnight at 4° C. to dissolve DNAs.

5 μl of an RNase (Sigma, E.C. 3.1.27.5) solution prepared beforehand at 10 mg/ml with sterilized water was added to the aforementioned DNA solution, and the mixture was incubated at 37° C. for 1 hour. 0.25 ml of phenol/chloroform (1/1) solution was added to the mixture, the mixture was gently stirred for 10 minutes, 0.25 ml of chloroform was further added to the mixture, and the mixture was gently stirred for 5 minutes. The mixture was subjected to refrigerated centrifugation at 4° C. and 6,000×g for 10 minutes, the aqueous layer of the upper layer was transferred to a new 2 ml volume microtube, 50 μl of 3 M sodium acetate aqueous solution and 1 ml of 99.5% cold ethanol were added to the mixture, and the mixture was gently stirred. The mixture was subjected to refrigerated centrifugation at 4° C. and 15,000×g for 10 minutes, the supernatant was removed, then the residue was washed with 0.4 ml of 70% cold ethanol, and the pellet was dried (the aforementioned procedure is also referred to as the "RNase treatment").

125 μl of TE buffer was added to the dried pellet, and the mixture was left overnight at 4° C. to dissolve DNAs and thereby obtain extracted DNAs. Absorbance values of the purified DNA solution was measured at 260 nm and 280 nm ($OD_{260}$, $OD_{280}$, $OD_{260}$ of 50 μg/ml DNA solution was 1.0, cell length: 1 cm), DNA concentration was calculated from $OD_{260}$, and purity of the purified DNA was estimated on the basis of $OD_{260}/OD_{280}$.

DNAs of *Listeria* were extracted by the method of Example 1, 1-3) Extraction of DNA.

1-4) Electrophoresis of PCR Amplification Products

The chromosomal DNAs extracted in 1-3) were subjected to electrophoresis by using 0.8% agarose gel. After completion of the electrophoresis, the agarose gel was immersed in a 1 μg/ml ethidium bromide aqueous solution for 20 minutes, and then washed twice with ion-exchanged water, and cleavage degree of the chromosomal DNAs was observed by using a UV transilluminator (wavelength: 254 nm).

2. Test Method (PCR Targeting 23S rRNA Gene and Electrophoresis)

2-1) Preparation of PCR Master Mix

A master mix (total volume: 50 μl) of the following composition was prepared.

Ex-Taq® (Takara Shuzo, catalog number: RR001B, TaKaRa Ex Taq enzyme): 0.25 μl
10×Ex-Taq® Buffer (Takara Shuzo, catalog number: RR001B): 5 μl
dNTP mixture (Takara Shuzo, catalog number: RR001B): 4 μl
  5 pmol/μl SEQ ID NO: 1 (23 S-F) DNA: 2.5 μl
  5 pmol/μl SEQ ID NO: 2 (23S-R) DNA: 2.5 μl
  5 pmol/μl SEQ ID NO: 3 (23S-MF) DNA: 2.5 μl
  5 pmol/μl SEQ ID NO: 4 (23S-MR) DNA: 2.5 μl
  2×SYBR® Green (cyanine dye) (BMA, catalog number: 50513): 10 μl
  Sterilized water: 15.75 μl
  Template DNA (15 ng/μl): 10 μl The primers of SEQ ID NOS: 1 and 2 are primers for amplifying substantially all the region of 23S rRNA, and they provide an amplification fragment of about 2840 bp mainly from gram-negative bacteria. The primers of SEQ ID NOS: 3 and 4 correspond to the center region of 23S rRNA, and they provide an amplification fragment of about 900 bp from gram-positive bacteria (also from gram negative bacteria).

2-2) PCR Thermal Cycle Profile for Amplification of 23S rRNA Gene

The PCR thermal cycle profile for amplification of the 23S rRNA gene of *Enterobacter* was as shown in Table 1.

TABLE 1

| Cycle | Repeats | Step | Retention time | Hold | Set (° C.) | Temperature elevation interval (° C.) |
|---|---|---|---|---|---|---|
| 1 | 1 | 1 | 03:00 | | 4 | |
| 2 | 1 | 1 | 00:30 | | 94 | |
| 3 | 40 | 1 | 00:20 | | 94 | |
| | | 2 | 00:30 | | 55 | |
| | | 3 | 02:30 | | 72 | |
| 4 | 1 | 1 | 03:00 | | 95 | |
| 5 | 350 | 1 | 00:08 | | 60 | 0.1 |
| 6 | | | | ∞ | 4 | |

The PCR thermal cycle profile for amplification of the 23S rRNA gene of *Listeria* was as shown in Table 2.

TABLE 2

| Cycle | Repeats | Step | Retention time | Hold | Set (° C.) | Temperature elevation interval (° C.) |
|---|---|---|---|---|---|---|
| 1 | 1 | 1 | 03:00 | | 4 | |
| 2 | 1 | 1 | 00:30 | | 94 | |
| 3 | 40 | 1 | 00:20 | | 94 | |
| | | 2 | 00:30 | | 46 | |
| | | 3 | 01:00 | | 72 | |
| 4 | 1 | 1 | 03:00 | | 95 | |
| 5 | 350 | 1 | 00:08 | | 60 | 0.1 |
| 6 | | | | ∞ | 4 | |

2-3) PCR

Each of the DNA solutions prepared in 1-3) was diluted to 15 ng/μl with TE buffer, and 10 μl of the diluted solution was used as a template DNA in 2-1). That is, 150 ng of the template DNA was contained in 50 μl of the PCR reaction mixture. As a negative control, 10 μl of TE buffer was used.

According to the PCR thermal cycle profile shown in 2-2) mentioned above, PCR and TM analysis (melting temperature analysis) of the amplification product were performed by using a real-time PCR apparatus i Cycler® (Biorad, model number: iQ). The threshold value (boundary value) of real-time PCR was set to a value obtained by multiplying the standard deviation SD of fluorescence amounts obtained with SYBR® Green (cyanine dye) for 0 to 10 cycles by 10. In each real-time PCR amplification curve, number of cycle showing a value exceeding the threshold value is referred to as "Ct value" hereafter.

3. Test Results

Figure 2:
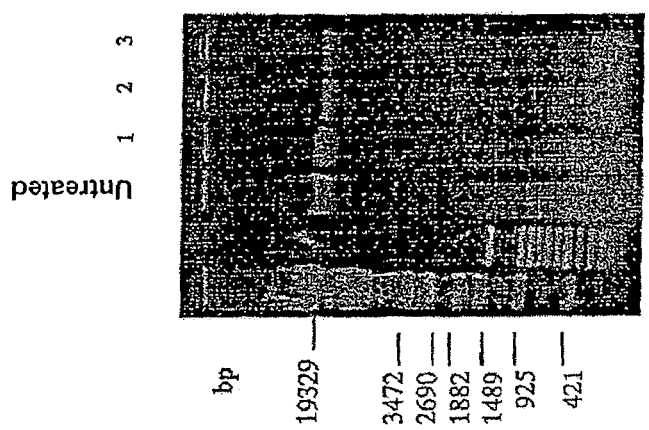
FIG. 2 Electrophoresis photographs showing influence of injured cell intracellular DNase on chromosomal DNA of *Enterobacter* (injured cells):
Non: Untreated,
1: Incubation at 37° C. for 24 hours,
2: Incubation at 37° C. for 48 hours,
3: Incubation at 37° C. for 72 hours.
Figure 3:
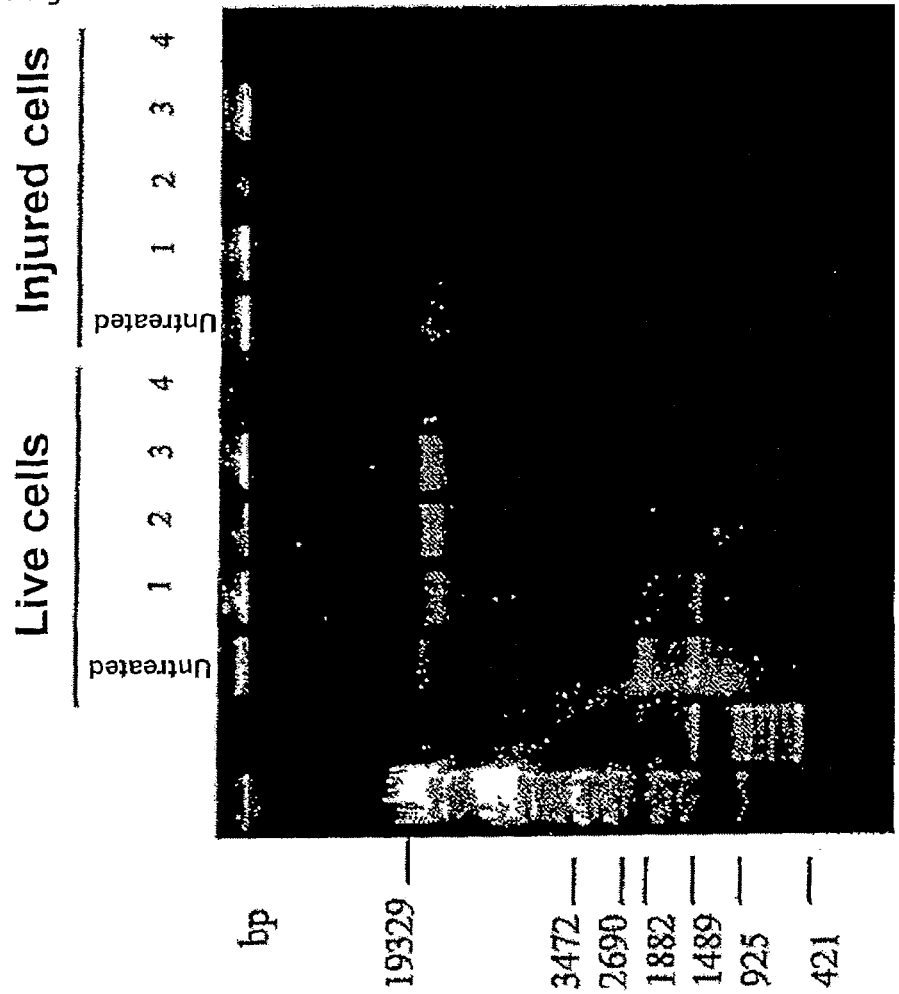
FIG. 3 Electrophoresis photographs showing influence of ciprofloxacin on chromosomal DNA of *Enterobacter* (live cells and injured cells):
Non: Untreated,
1: Incubation at 37° C. for 1.5 hours,
2: Incubation at 37° C. for 3.5 hours,
3: Incubation at 37° C. for 5 hours,
4: Incubation at 37° C. for 72 hours.
Figure 4:
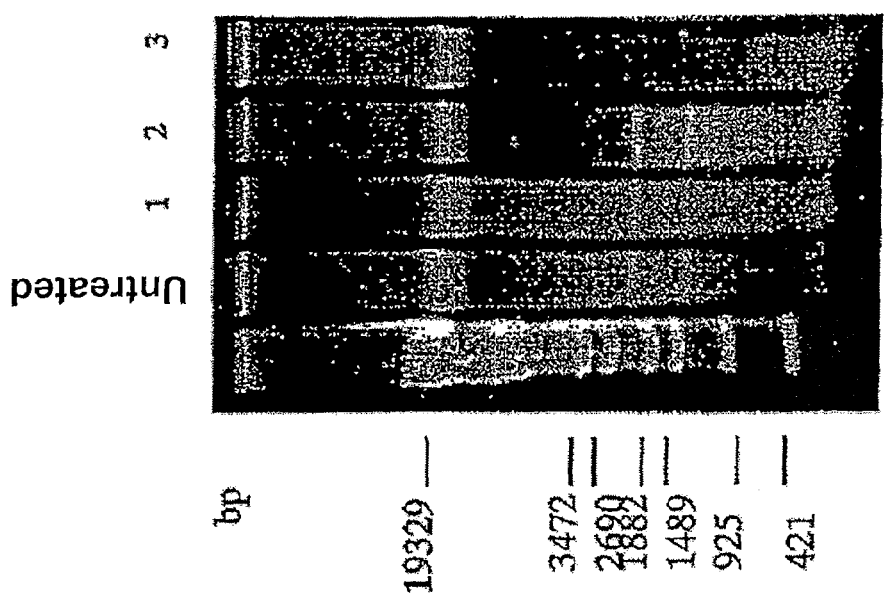
FIG. 4 Electrophoresis photographs showing influence of injured cell intracellular DNase on chromosomal DNA of *Listeria* (injured cells):
Non: Untreated,
1: Incubation at 30° C. for 24 hours,
2: Incubation at 30° C. for 48 hours,
3: Incubation at 30° C. for 72 hours.
Figure 5:
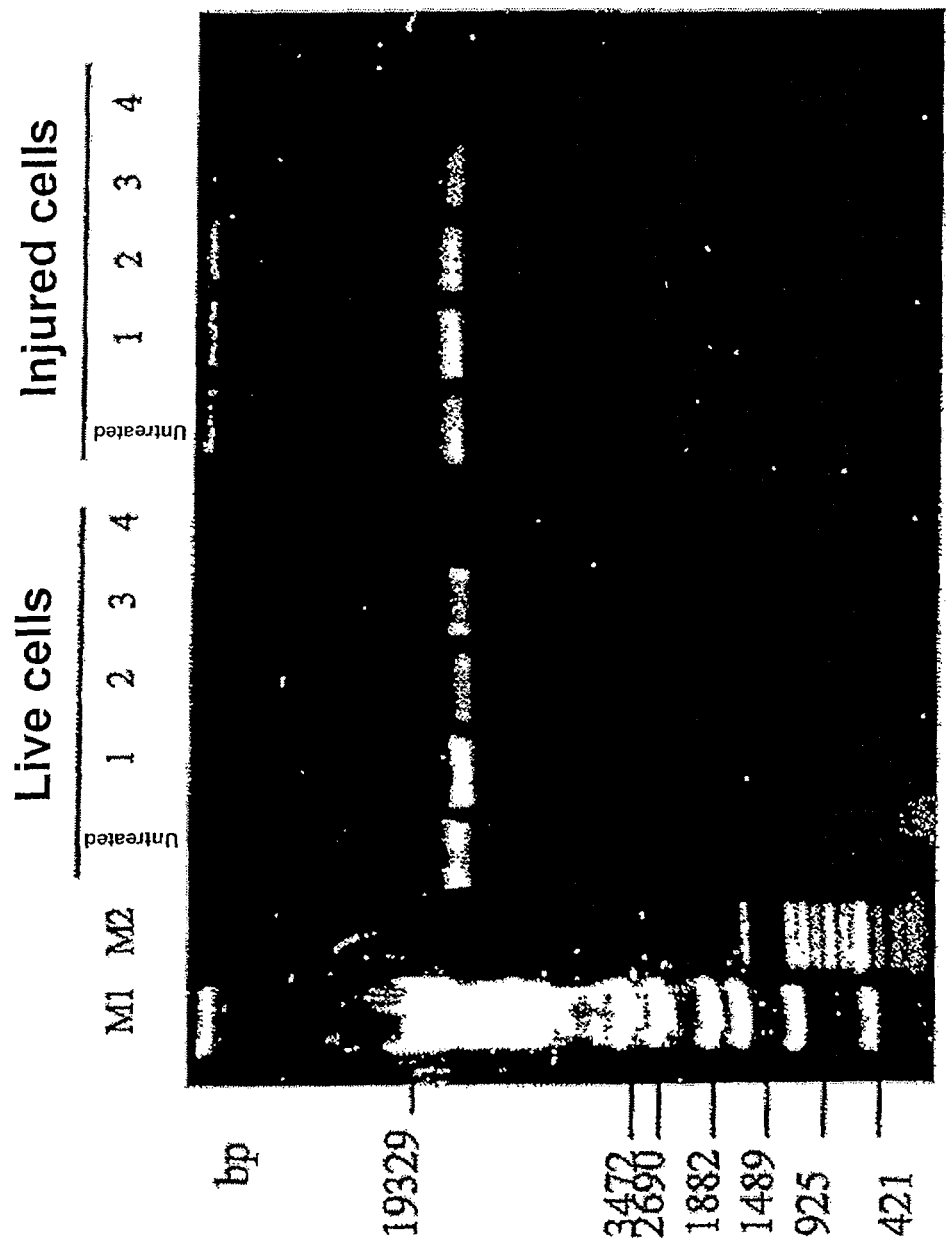
FIG. 5 Electrophoresis photographs showing influence of ciprofloxacin on chromosomal DNA of *Listeria* (live cells and injured cells):
Non: Untreated,
1: Incubation at 30° C. for 1.5 hours,
2: Incubation at 30° C. for 3.5 hours,
3: Incubation at 30° C. for 5 hours,
4: Incubation at 30° C. for 72 hours.

The test results of this example are shown in FIGS. 2 to 11. FIG. 2 shows influence of intracellular DNase on chromosomal DNA of *Enterobacter* (injured cells). FIG. 3 shows influence of ciprofloxacin on chromosomal DNAs of the same bacterium (live cells and injured cells). FIG. 4 shows influence of injured cell intracellular DNase on chromosomal DNA of *Listeria* (injured cells). FIG. 5 shows influence of ciprofloxacin on chromosomal DNAs of the same bacterium (live cells and injured cells).

Figure 6:
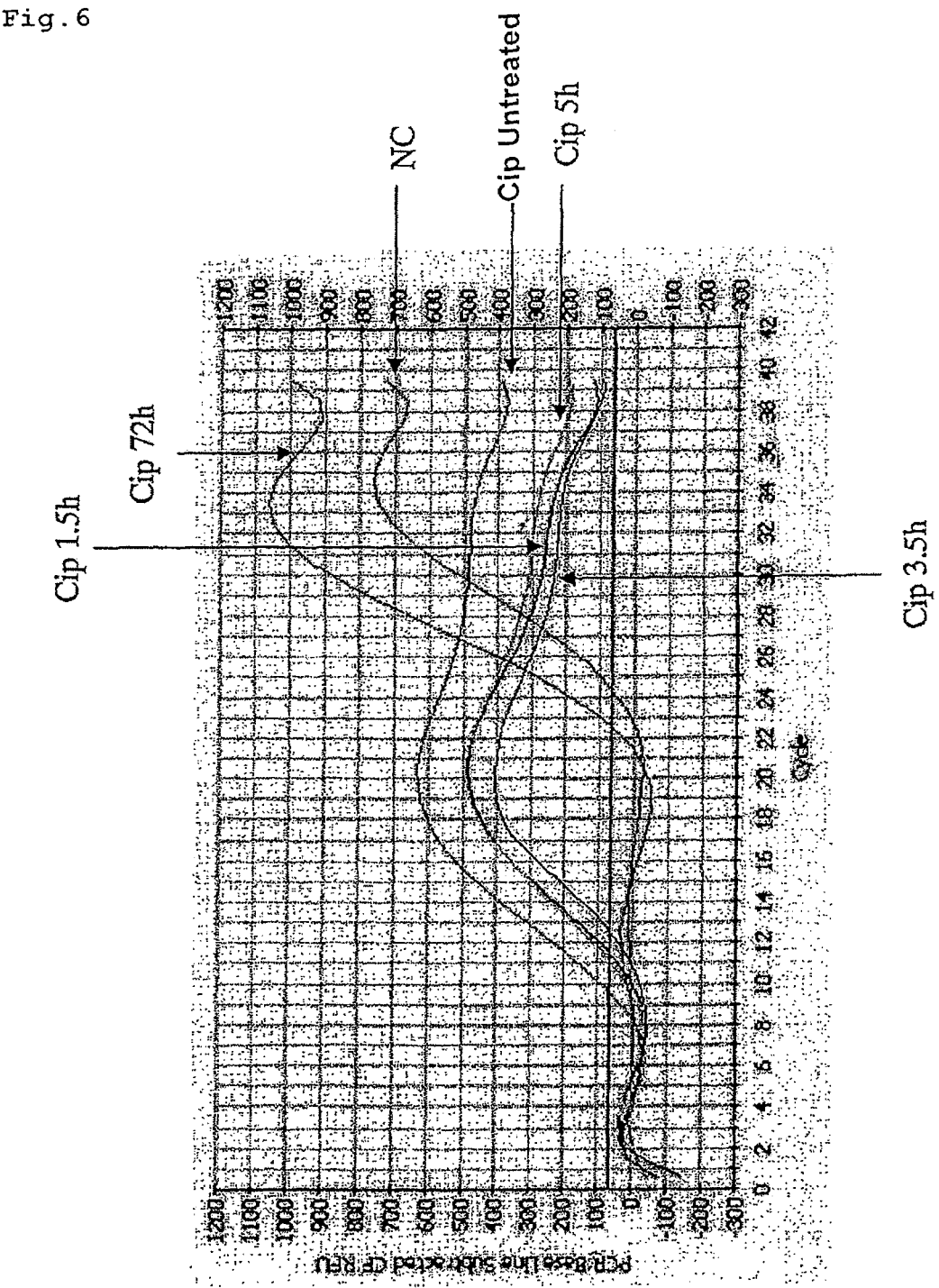
FIG. 6 Amplification curve in real-time PCR targeting the 23S rRNA gene of *Enterobacter* (live cells) treated with ciprofloxacin (halftone photograph).
Figure 7:
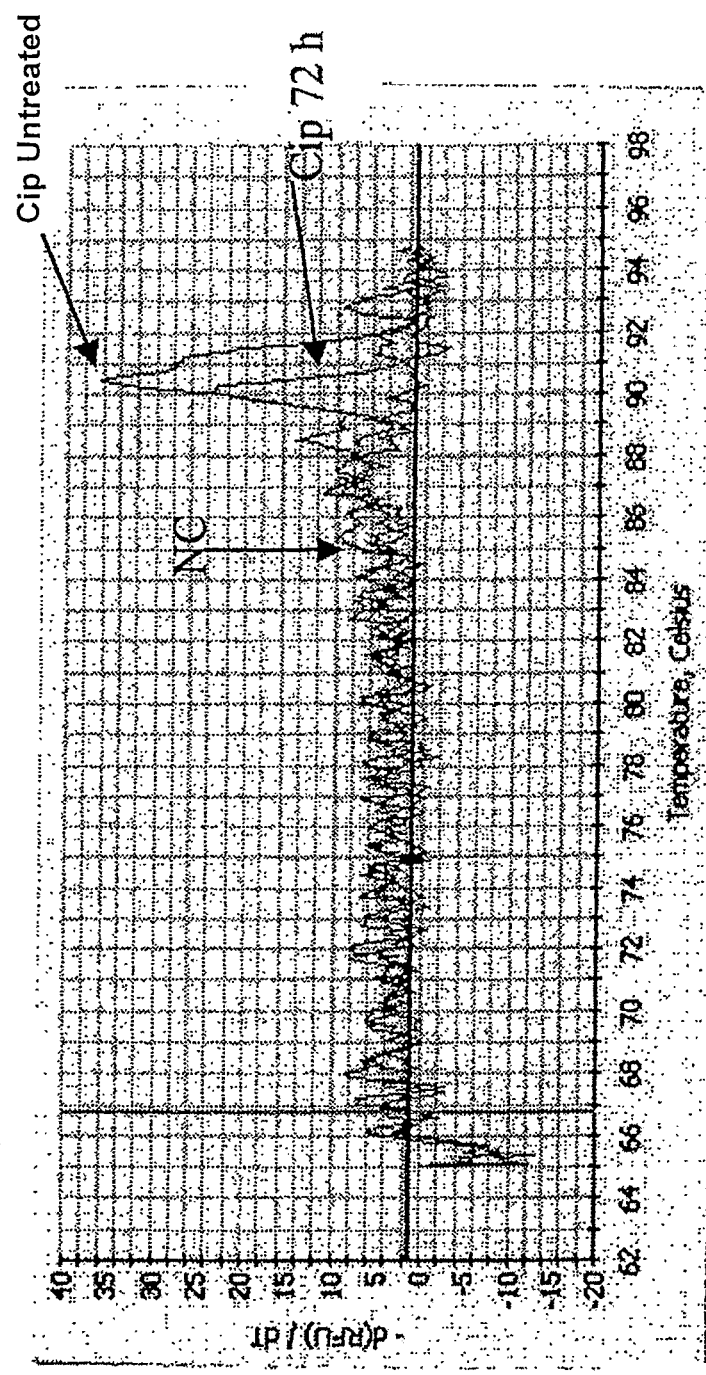
FIG. 7 TM pattern of amplification product in real-time PCR targeting the 23S rRNA gene of *Enterobacter* (live cells) treated with ciprofloxacin (halftone photograph).
Figure 8:
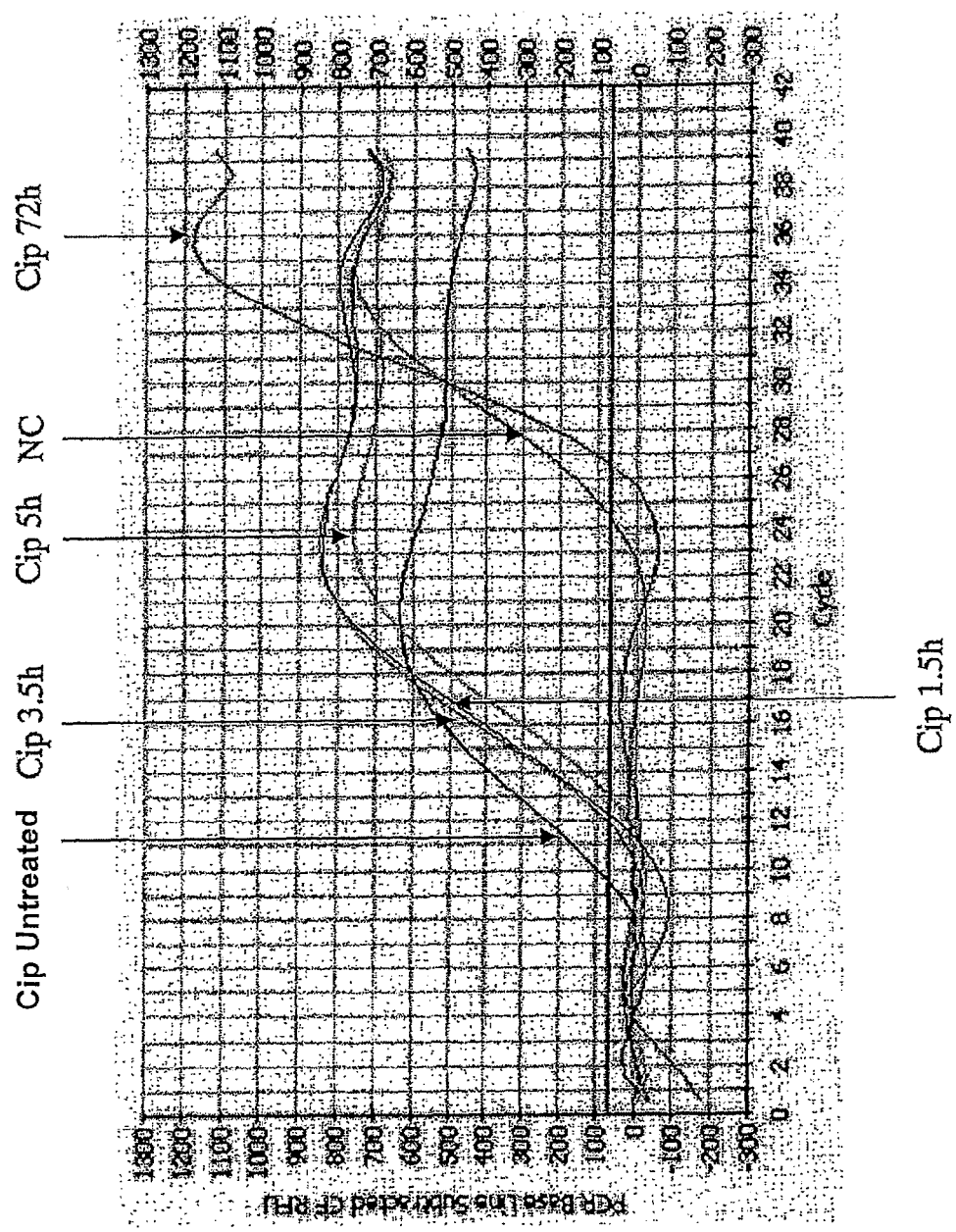
FIG. 8 Amplification curve in real-time PCR targeting the 23S rRNA gene of *Enterobacter* (injured cells) treated with ciprofloxacin (halftone photograph).
Figure 9:
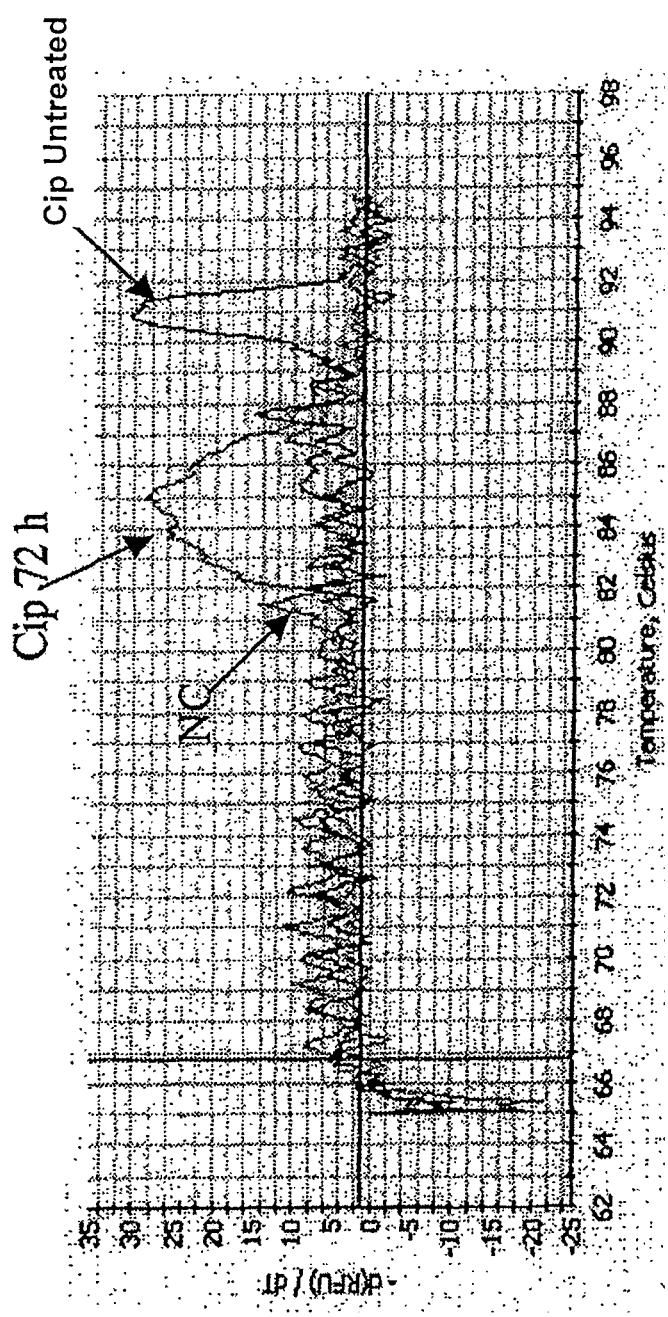
FIG. 9 TM pattern of amplification product in real-time PCR targeting the 23S rRNA gene of *Enterobacter* (injured cells) treated with ciprofloxacin (halftone photograph).
Figure 10:
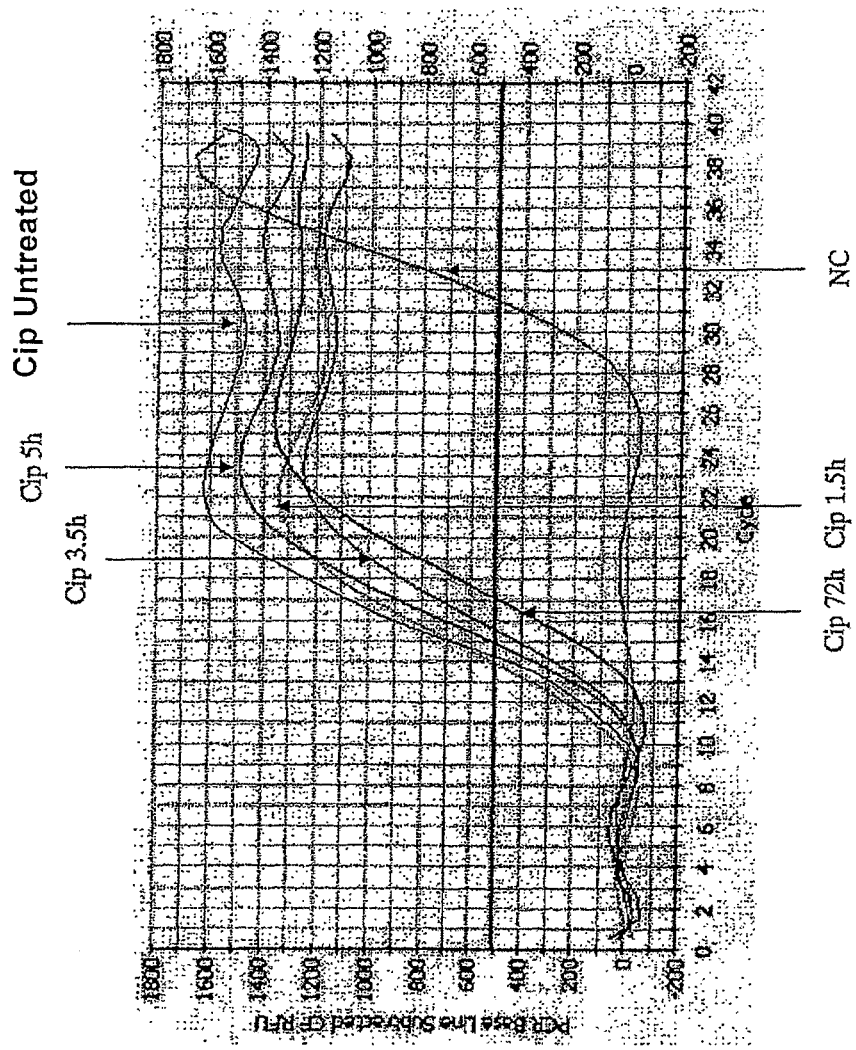
FIG. 10 Amplification curve in real-time PCR targeting the 23S rRNA gene of *Listeria* (live cells) treated with ciprofloxacin (halftone photograph).
Figure 11:
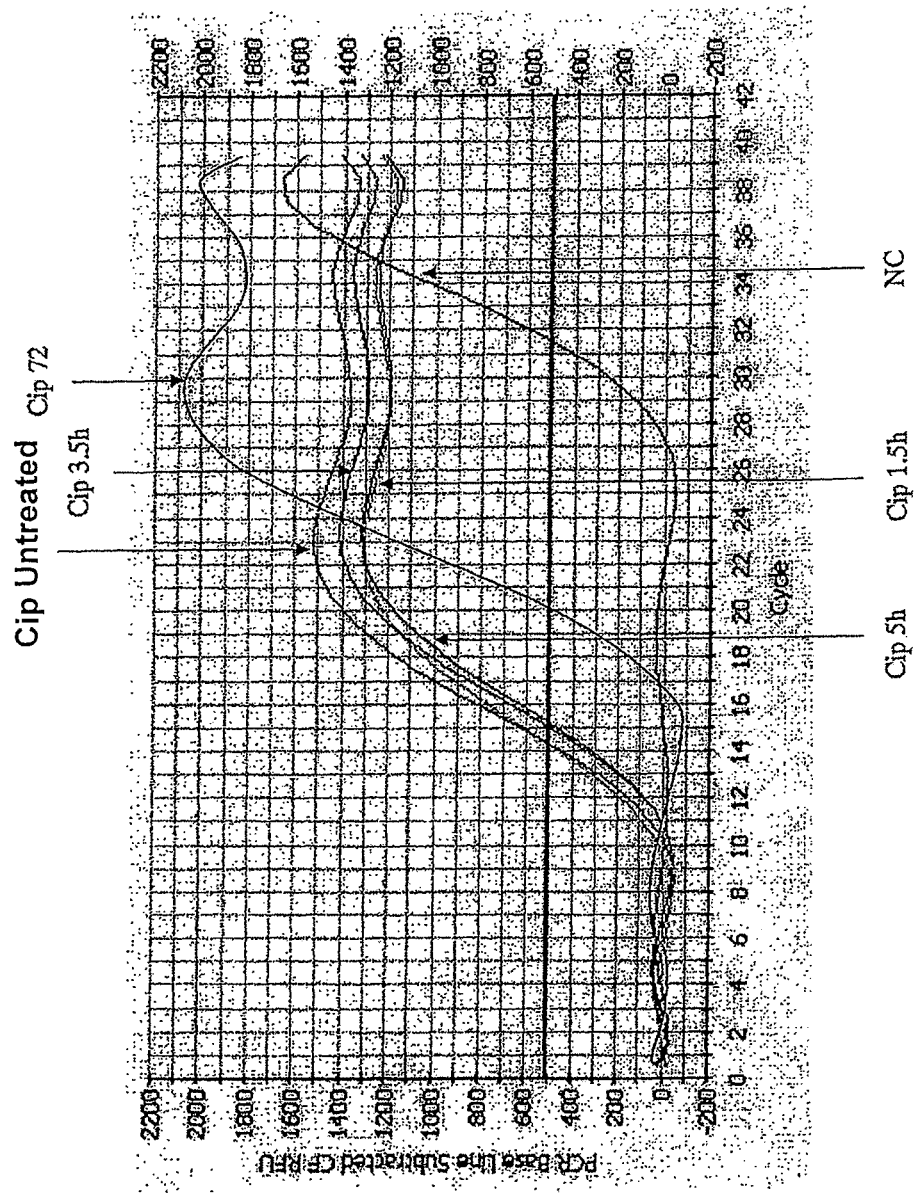
FIG. 11 Amplification curve in real-time PCR targeting the 23S rRNA gene of *Listeria* (injured cells) treated with ciprofloxacin (halftone photograph).

Further, FIG. 6 shows an amplification curve for real-time PCR targeting the 23S rRNA gene of *Enterobacter* live cells treated with ciprofloxacin. FIG. 7 shows results of TM pattern analysis of the amplification product mentioned in FIG. 6. Similarly, the real-time PCR curve and the result of the TM pattern analysis of injured cell of the same bacterium treated with the same drug are shown in FIGS. 8 and 9, respectively. Furthermore, the real-time PCR curve of live cells and injured cell of *Listeria* treated with the same drug are shown in FIGS. 10 and 11, respectively.

From the results shown in FIG. 2, it was confirmed that the injured cell chromosomal DNAs were slightly cleaved by DNase retained in *Enterobacter* injured cells over 72 hours. However, as shown in FIG. 3, even when ciprofloxacin was made to act on injured cells for 1.5 to 5 hours, the DNA cleavage phenomenon was also observed at a degree markedly higher than that observed with the aforementioned DNase. In the case of the live cells, the long chromosomal DNA fragment around 19329 bp conversely increased, and thus it was confirmed that by the action of ciprofloxacin for a short period of time, the chromosomal DNAs of injured cells were more cleaved with the aid of the bacterial DNA gyrase compared with live cells.

As shown in FIG. 4, as for the injured cell chromosomal DNAs, the DNA cleavage phenomenon caused by intracellular DNase of *Listeria* injured cells was hardly observed for the long fragment around 19329 bp derived from the chromosomal DNAs even after 72 hours. However, as shown in FIG. 5, when ciprofloxacin was made to act on the injured cells for 72 hours, a markedly severer DNA cleavage phenomenon caused by the aforementioned DNase was observed. It is construed that the action and effect of ciprofloxacin on live cells are the same.

Further, when ciprofloxacin was made to act for 72 hours, PCR was markedly suppressed for both the live cells and injured cells of *Enterobacter*. However, as shown by calculations of Ct (live cells, 72 hours of Cip)–Ct (live cells, No Cip)=13 and Ct (injured cells, 72 hours of Cip)–Ct (injured cells, No Cip)=17, PCR was more suppressed for the injured cells. That is, when PCR was terminated after 27 cycles, the result of PCR performed for the live cells was determined to be positive, and the result of PCR performed for the injured cells was determined to be negative. Therefore, it was confirmed that live cells and injured cells could be distinguished by using ciprofloxacin. As also for *Listeria*, when PCR was terminated after 20 cycles, the result of PCR performed for the live cells was similarly determined to be positive, and the result of PCR performed for the injured cells was similarly determined to be negative, as shown in FIG. 10 and FIG. 11, respectively. Therefore, it was confirmed that live cells and injured cells of *Listeria* could also be distinguished by using the drug.

On the basis of the TM pattern analysis of the PCR amplification products of the chromosomal DNAs of *Enterobacter sakazakii* live cells and injured cells on which ciprofloxacin was made to act for 72 hours as shown in FIGS. 7 and 9, it is estimated that the PCR amplification product for the live cells corresponds to the 23S rRNA gene as the target, whereas the PCR amplification product for the injured cells is not the targeted amplification product. It is considered that a partial region of the 23S rRNA gene was amplified as the PCR amplification product for the injured cell as a result of multiple cleavages caused in the 23S rRNA gene of the template DNA. As described above, it was demonstrated that live cells and injured cells can be distinguished by PCR using a ciprofloxacin treatment.

Example 3

Analysis was performed by PCR targeting the 16S rRNA gene or the 23S rRNA gene using chromosomal DNAs of live cells and injured cells of microorganisms treated with EMA.

1. Preparation of Samples 1-1) Preparation of Gram-Negative Bacterium (Live Cell and Injured Cell) Suspensions

*Escherichia coli* DH5α (henceforth also referred to as "*Escherichia coli*"), *Citrobacter koseri* (*Citrobacter koseri* JCM 1658, henceforth also referred to as "*Citrobacter*"), *Salmonella enteritidis* (*Salmonella enteritidis* IID 604, henceforth also referred to as "*Salmonella*"), and *Klebsiella oxytoca* (*Klebsiella oxytoca* JCM 1665, henceforth also referred to as "*Klebsiella*") were each cultured at 37° C. by using the BHI broth, 40 ml of the culture medium in which the cells were at the logarithmic phase was subjected to refrigerated centrifugation at 4° C. and 8,000×g for 15 minutes, and the supernatant was removed. Then, 40 ml of physiological saline was added to the cells, and the mixture was sufficiently stirred, and subjected to similar refrigerated centrifugation, the supernatant was removed, and then 10 ml of physiological saline was added to the cells to prepare a live cell suspension. The live cell counts of these live cell suspensions were *Escherichia coli*: $3.2 \times 10^8$ cfu/ml, *Citrobacter*: $6.7 \times 10^7$ cfu/ml, *Salmonella*: $1.9 \times 10^8$ cfu/ml, and *Klebsiella*: $4.8 \times 10^8$ cfu/ml.

Further, 1 ml each of the aforementioned live cell suspensions were put into 1.5 ml microtubes, and the tubes were immersed in boiling water for 50 seconds, and rapidly cooled with ice water to prepare injured cell suspensions.

1-2) Preparation of Gram-Positive Bacterium (Live Cells and Injured Cells) Suspensions

*Bacillus cereus* (*Bacillus cereus* JCM 2152, henceforth also referred to as "*Bacillus*"), and *Staphylococcus epidermidis* (*Staphylococcus epidermidis* KD, henceforth also referred to as "*Staphylococcus*") were cultured at 37° C., and *Listeria monocytogenes* (*Listeria monocytogenes* JCM 2873, henceforth also referred to as "*Listeria*") was cultured at 30° C., respectively, in the BHI broth, 40 ml of each culture medium in which the cells were at the logarithmic phase (trophozoite cells for *Bacillus*) was subjected to refrigerated centrifugation at 4° C. and 8,000×g for 15 minutes, and the supernatant was removed. Then, 40 ml of physiological saline was added to the cells, and the mixture was sufficiently stirred, and subjected to similar refrigerated centrifugation, the supernatant was removed, and then 10 ml of physiological saline was added to the cells to prepare a live cell suspension. The live cell counts of these live cell suspensions were *Bacillus*: $3.0 \times 10^7$ cfu/ml, *Listeria*: $1.3 \times 10^8$ cfu/ml, and *Staphylococcus*: $1.1 \times 10^6$ cfu/ml.

Further, 1 ml each of the aforementioned live cell suspensions were put into 1.5 ml microtubes, and the tubes were immersed in boiling water for 50 seconds, and rapidly cooled with ice water to prepare injured cell suspensions.

2. Test Method 2-1) EMA Treatment and Visible Light Irradiation Steps

10 μl of an EMA solution prepared at a concentration of 1000 μg/ml by dissolving EMA (Sigma, catalog number: E2028) in sterilized water, and filtering the solution through a 0.45-μm microfilter was added to each of the suspensions of the gram-negative bacteria (live cells and injured cells) and gram-positive bacteria (live cells and injured cells) in a volume of 1 ml, and the mixture was left at 4° C. for 30 minutes under light shielding. Then, the suspension was placed on ice, and irradiated with visible light of 500 W from a lamp (FLOOD PRF, 100 V, 500 W, Iwasaki Electric Co., Ltd.) disposed at a distance of 20 cm from the suspension for 10 minutes. The above steps of adding the EMA solution and irradiating visible light may also be referred to as the "EMA treatment". Separately, 10 μl of sterilized water was added to 1 ml of each suspension of the gram-negative bacteria (live cells and injured cells) and gram-positive bacteria (live cells and injured cells) instead of the EMA solution, and then the mixture was subjected to the same procedure used for the aforementioned EMA treatment.

2-2) DNA Extraction

Microtubes containing the live cells and injured cells of the gram-negative bacteria and gram-positive bacteria (EMA-untreated and EMA-treated for each) were subjected to refrigerated centrifugation at 4° C. and 15,000×g for 10 minutes. 990 µl of physiological saline was added to each microtube, and the mixture was sufficiently stirred. Then, the total volume of the mixture was transferred to a 2 ml microtube, and subjected to refrigerated centrifugation at 4° C. and 15,000×g for 10 minutes, and the supernatant was removed. Thereafter, DNAs were extracted, DNA concentration was measured, and purity was evaluated according to the method of Example 1, 1-3) Extraction of DNA.

3. PCR Targeting 16S rRNA Gene or 23S rRNA Gene 3-1) Preparation of PCR Master Mix A master mix (total volume: 50 µl) of the following composition was prepared.

Ex-Taq® (Takara Shuzo, catalog number: RR001B): 0.25 µl

10×Ex-Taq® Buffer (Takara Shuzo, catalog number: RR001B, TaKaRa Ex Taq enzyme): 5 µl dNTP mixture (Takara Shuzo, catalog number: RR001B): 4 µl 5 pmol/µl SEQ ID NO: 1 (23 S-F) DNA: 2.5 µl 5 pmol/µl SEQ ID NO: 2 (23S-R) DNA: 2.5 µl 5 pmol/µl SEQ ID NO: 3 (23S-MF) DNA: 2.5 µl 5 pmol/µl SEQ ID NO: 4 (23S-MR) DNA: 2.5 µl 5 pmol/µl SEQ ID NO: 5 (16S-F) DNA: 2.5 µl 5 pmol/µl SEQ ID NO: 6 (16S-R) DNA: 2.5 µl 2×SYBR® Green (cyanine dye) (BMA, catalog number: 50513): 10 µl Sterilized water: 15.75 µl Template DNA (15 ng/µl): 10 µl 3-2) PCR Thermal Cycle Profile for Amplification of 16S rRNA Gene The PCR thermal cycle profile for amplification of the 16S rRNA gene of each bacterium was as shown in Table 3.

TABLE 3

| Cycle | Repeats | Step | Retention time | Hold | Set (° C.) | Temperature elevation interval (° C.) |
|---|---|---|---|---|---|---|
| 1 | 1 | 1 | 03:00 | | 4 | |
| 2 | 1 | 1 | 00:30 | | 94 | |
| 3 | 40 | 1 | 00:20 | | 94 | |
| | | 2 | 00:30 | | 55 | |
| | | 3 | 01:30 | | 72 | |
| 4 | 1 | 1 | 03:00 | | 95 | |
| 5 | 350 | 1 | 00:08 | | 60 | 0.1 |
| 6 | | | | ∞ | 4 | |

3-3) PCR Thermal Cycle Profile for Amplification of 23S rRNA Gene

The PCR thermal cycle profile for amplification of the 23S rRNA gene of each bacterium was as shown in Table 4 (gram-negative bacteria) or Table 5 (gram-positive bacteria).

TABLE 4

| Cycle | Repeats | Step | Retention time | Hold | Set (° C.) | Temperature elevation interval (° C.) |
|---|---|---|---|---|---|---|
| 1 | 1 | 1 | 03:00 | | 4 | |
| 2 | 1 | 1 | 00:30 | | 94 | |
| 3 | 40 | 1 | 00:20 | | 94 | |
| | | 2 | 00:30 | | 46 or 55 | |
| | | 3 | 02:30 | | 72 | |
| 4 | 1 | 1 | 03:00 | | 95 | |
| 5 | 350 | 1 | 00:08 | | 60 | 0.1 |
| 6 | | | | ∞ | 4 | |

TABLE 5

| Cycle | Repeats | Step | Retention time | Hold | Set (° C.) | Temperature elevation interval (° C.) |
|---|---|---|---|---|---|---|
| 1 | 1 | 1 | 03:00 | | 4 | |
| 2 | 1 | 1 | 00:30 | | 94 | |
| 3 | 40 | 1 | 00:20 | | 94 | |
| | | 2 | 00:30 | | 46 | |
| | | 3 | 01:00 | | 72 | |
| 4 | 1 | 1 | 03:00 | | 95 | |
| 5 | 350 | 1 | 00:08 | | 60 | 0.1 |
| 6 | | | | ∞ | 4 | |

3-4) PCR

Each of the DNA solutions prepared in 2-2) was diluted to 15 ng/µl with TE buffer, and 10 µl of the diluted solution was used as a template DNA in 3-1). That is, 150 ng of the template DNA was contained in 50 µl of the PCR reaction mixture. As a negative control, 10 µl of TE buffer was used.

According to the PCR thermal cycle profile shown in 3-2) or 3-3) mentioned above, PCR and TM analysis (melting temperature analysis) of the amplification product were performed by using a real-time PCR apparatus i Cycler® (Biorad, model number: iQ). The threshold value (boundary value) and the Ct value of real-time PCR were calculated in the same manner as that of Example 2, 2-3).

3-5) Agarose Gel Electrophoresis

From Seakem GTG agarose (FMC, catalog number: 50070) and TAE buffer (4.84 g/L of Tris, 1.142 ml/L of acetic acid, 0.149 g/L of EDTA.2Na), 0.8% agarose gel was prepared, and λ-EcoT14I digest (Takara Shuzo, Code: 3401) and 100 bp DNA Ladder (Takara Shuzo, Code: 3407A) were used as markers. For each of the gram-negative bacteria and gram-positive bacteria, 10 µl of the PCR solution was dispensed into a well, and subjected to electrophoresis. When bromophenol blue (BPB) migrated about 90% in the gel, the electrophoresis was terminated.

The gel on which the electrophoresis was performed was immersed in 1 µg/ml ethidium bromide aqueous solution for 20 minutes and washed twice with ion-exchanged water, and then the PCR amplification product was observed by using a UV transilluminator (254 nm).

4. Test Results

Figure 12:
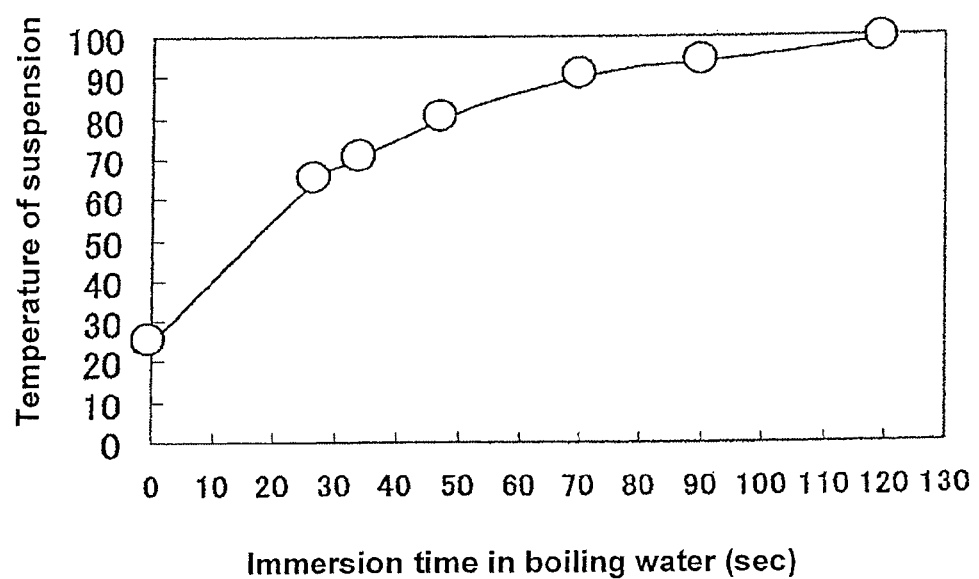
FIG. 12 Graph showing the relationship of immersion time in boiling water of a microtube containing cell suspension and temperature of the suspension in the microtube.

Change in temperature of bacterium suspension over time observed when a 1.5 ml microtube containing 1 ml of the bacterium suspension is immersed in boiling water is shown in FIG. 12. It can be seen from the relationship shown in FIG. 12 that the heat treatment by immersion in boiling water for 50 seconds used in the preparation of injured cell suspensions is a slightly stronger heat treatment compared with the high temperature short time pasteurization at 72 to 75° C. for 15 to 16 seconds (HTST pasteurization), and therefore it corresponds to a heat treatment equivalent to the ultrahigh temperature pasteurization (UHT pasteurization).

Figure 13:
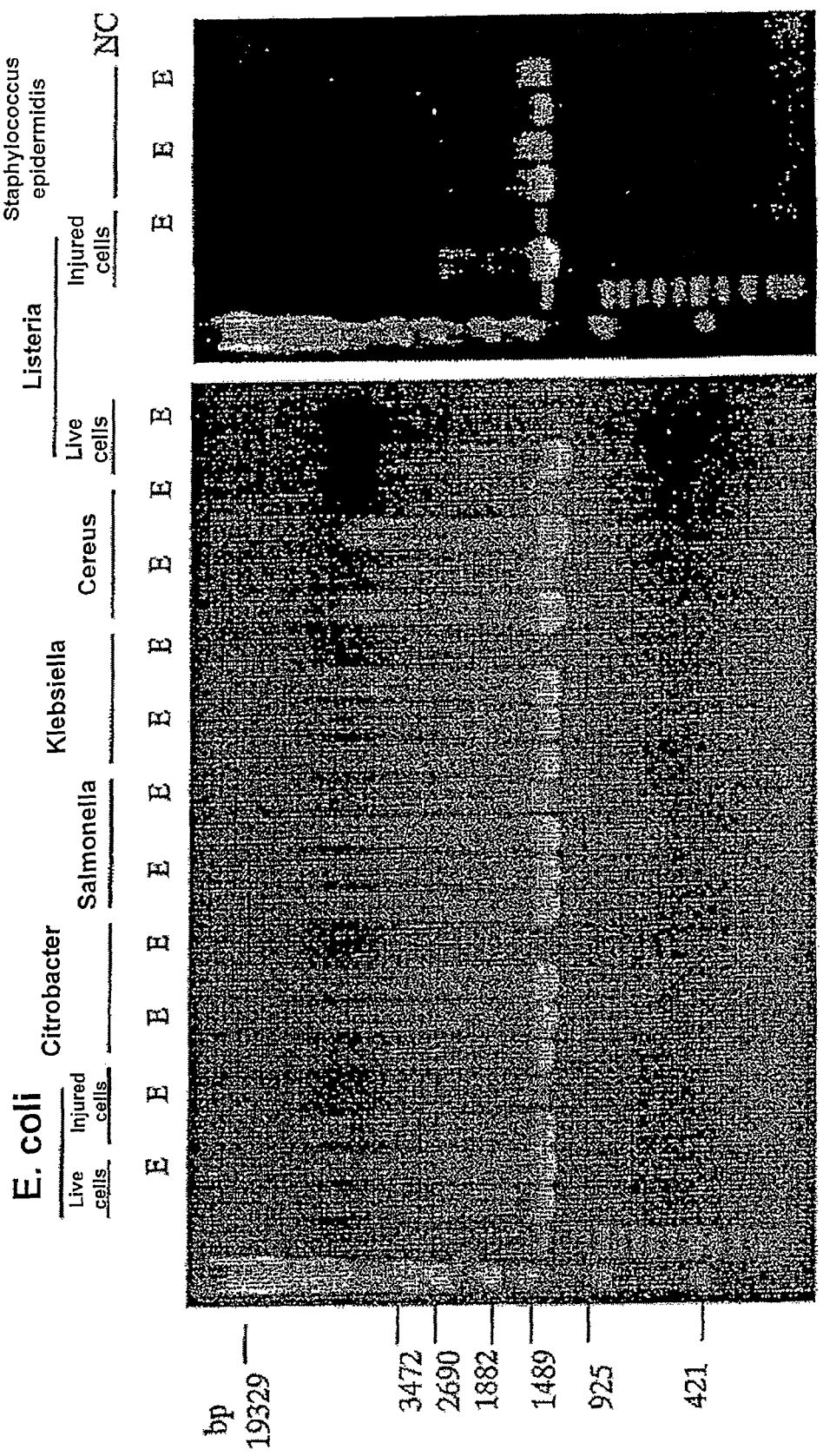
FIG. 13 Electrophoresis photographs showing results of PCR gene amplification targeting the 16S rRNA gene of seven kinds of bacteria (live cells and injured cells) treated or not treated with EMA, which are shown in the order of live cell suspension not treated with EMA, live cell suspension treated with EMA, injured cell suspension not treated with EMA, and injured cell suspension treated with EMA, for each bacterium. The same shall apply to FIGS. 14 and 15.
Figure 14:
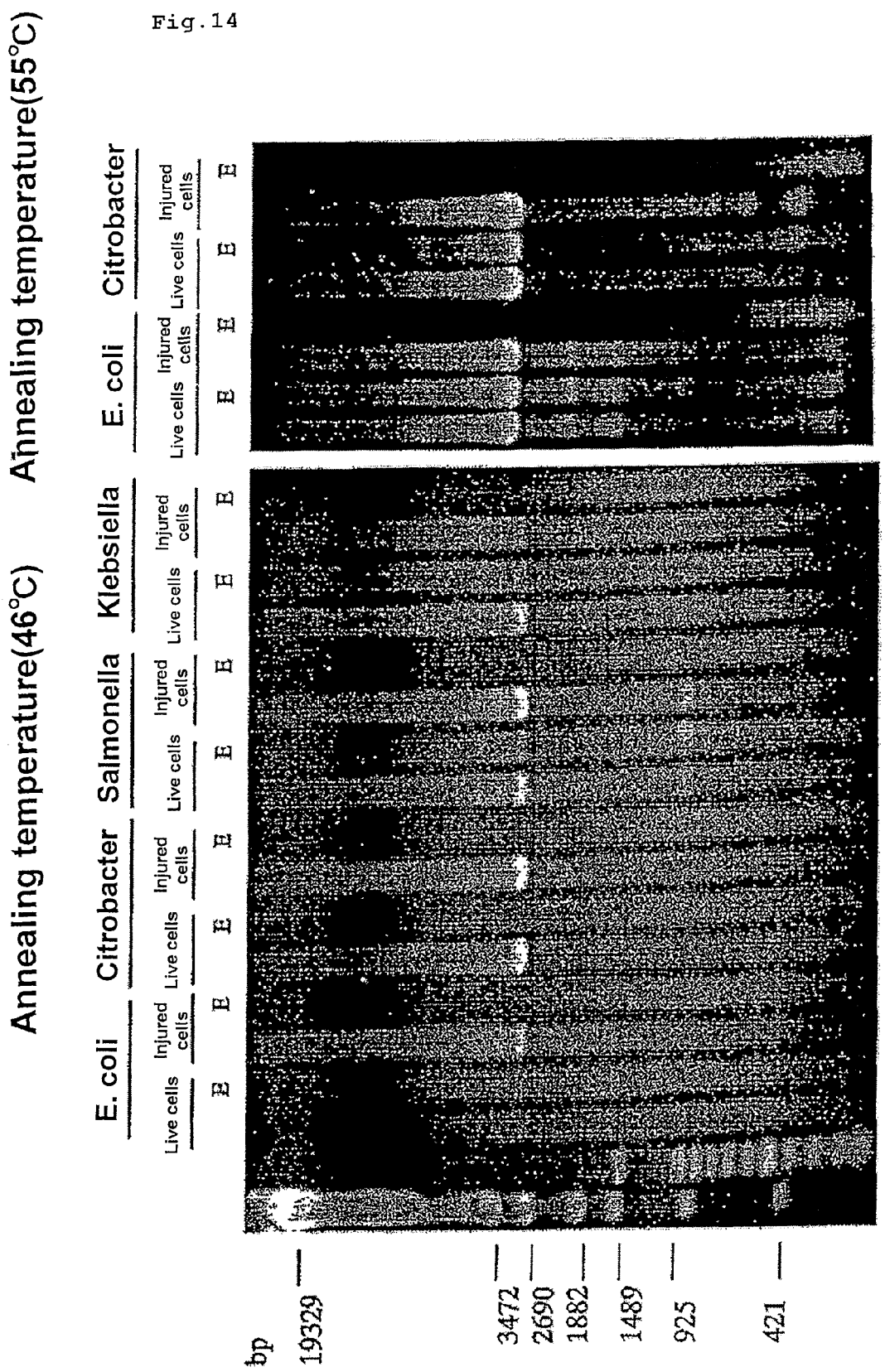
FIG. 14 Electrophoresis photographs showing results of PCR gene amplification targeting the 23S rRNA genes of four kinds of bacteria (live cells and injured cells) treated or not treated with EMA.
Figure 15:
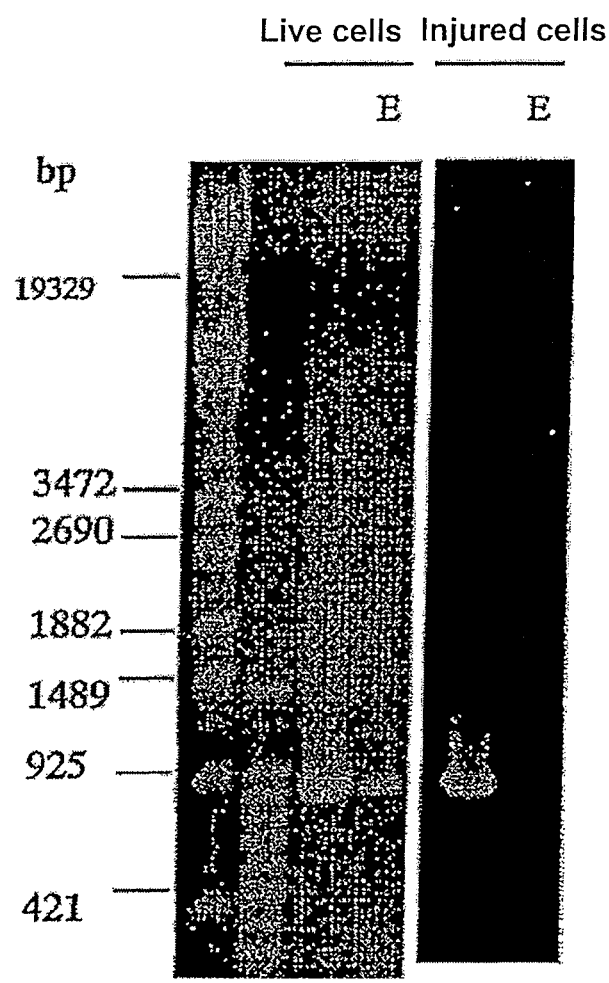
FIG. 15 Electrophoresis photographs showing results of PCR gene amplification targeting the 23S rRNA gene of *Listeria* (live cells and injured cells) treated or not treated with EMA.

The results of distinction of live cells and injured cells using the 16S rRNA gene as the target are shown in FIG. 13, and the results of distinction of live cells and injured cells using the 23S rRNA gene as the target are shown in FIGS. 14 and 15, respectively. In FIGS. 13 to 15, the PCR solutions of each bacterium were loaded on the gel in the order of those for the EMA-untreated live cell suspension, EMA-treated live cell suspension, EMA-untreated injured cell suspension, and EMA-treated injured cell suspension.

As shown in FIG. 13, when the 16S rRNA gene was used as the target, no PCR amplification product was observed for EMA-treated injured cells of *Citrobacter* and *Klebsiella*, and therefore clear distinction of live cells and injured cells was possible. For the other bacteria, amplification products were observed for the EMA-treated injured cells, and therefore distinction of live cells and injured cells was indefinite.

On the other hand, from the results shown in FIGS. 14 and 15, it was revealed that when the 23S rRNA gene was used as the target, live cells and injured cells could be clearly distinguished by using the EMA treatment for both the gram-negative bacteria and gram-positive bacteria. When a test sample containing bacterial injured cells at a level of $10^8$ cfu/ml as the sample background and 150 ng of a template DNA in a volume of 50 µl were used for PCR, PCR of the injured cells was completely inhibited, whereas PCR for live cells was not substantially completely inhibited. Moreover, it is considered that PCR for injured cells can be completely inhibited also for cow's milk containing $10^5$ to $10^7$ cfu/ml and live cells of a low concentration can be detected. Therefore, the method can be applied to a screening test for general bacteria in food sanitation inspection. Furthermore, in the case of a patient with sepsis and hepatic function disorder, it is possible that live cells and injured cells may exist at a high concentration of $10^4$ cfu/ml or higher in blood, and also in such a case, only live cells can be quickly detected according to the present invention.

Example 4

A pathogenic bacterium was treated with EMA and a topoisomerase poison or a DNA gyrase poison, and live cells and injured cells thereof were distinguished by PCR targeting a pathogenic gene.
1. Preparation of Bacterial Culture (Live Cells)
Live cell suspension and injured cell suspension of *Listeria* (*Listeria monocytogenes* JCM 2873) were prepared in the same manner as that of Example 1. The live cell count of the live cell suspension was $1.3 \times 10^8$ cfu/ml
2. Test Method
2-1) EMA Treatment and Visible Light Irradiation Steps
Each of the live cell suspension and injured cell suspension of *Listeria* prepared above was subjected to the EMA treatment and visible light irradiation in the same manner as that of Example 3. EMA is likely to penetrate into cells of gram positive bacteria, which do not have outer membranes, and even if the cells are live cells of which cell walls are not injured. Therefore, the time for leaving the suspension at 4° C. under light shielding after the addition of EMA was shortened to 5 minutes, and the visible light irradiation time was also shortened to 5 minutes. Further, 10 µl of sterilized water was also added to each of the live cell suspension and the injured cell suspension instead of the EMA solution, and the mixture was then subjected to the same treatments.

2-2) Topoisomerase Poison or DNA Gyrase Poison Treatment Step

After completion of the aforementioned EMA treatment and visible light irradiation steps, a microtube containing each treated suspension was subjected to refrigerated centrifugation at 4° C. and 15,000×g for 10 minutes, and the supernatant was removed. 1 ml of physiological saline was added to the cells, and the mixture was sufficiently stirred, and subjected to refrigerated centrifugation of the same condition. The supernatant was removed, then 1 ml of physiological saline was added to the cells, and the mixture was sufficiently stirred. As described above, 1 tube of 1 ml EMA-untreated live cell suspension, 7 tubes of 1 ml EMA-treated live cell suspension, 1 tube of 1 ml EMA-untreated injured cell suspension, and 7 tubes of 1 ml EMA-treated injured cell suspension were prepared.

The EMA-treated live cell and injured cell suspensions were divided into 6 sets, each of which consisted of 1 tube of the live cell suspension and 1 tube of injured cell suspension. Ciprofloxacin (0.5 mg/ml, dissolved with physiological saline) in a volume of 8 µl that is a DNA gyrase poison was added to the suspensions of the first set, camptothecin (1 mg/ml, dissolved in dimethyl sulfoxide) in a volume of 10 µl that is a topoisomerase poison was added to the suspensions of the second set, etoposide (1 mg/ml, dissolved in dimethyl sulfoxide) in a volume of 10 µl that is a topoisomerase poison was added to the suspensions of the third set, ellipticine (0.1 mg/ml, dissolved in dimethyl sulfoxide) in a volume of 5 µl that is a topoisomerase poison was added to the suspensions of the forth set, mitoxantrone (0.1 mg/ml, dissolved in dimethyl sulfoxide) in a volume of 10 µl that is a topoisomerase poison was added to the suspensions of the fifth set, and amsacrine (1 mg/ml, dissolved in dimethyl sulfoxide) in a volume of 10 µl that is a topoisomerase poison was added to the suspensions of the sixth set, respectively. Each sample was incubated at 30° C. for 30 minutes, the total volume of the sample was transferred into a 2 ml microtube and subjected to refrigerated centrifugation at 4° C. and 15,000×g for 10 minutes, and the supernatant was removed.

2-3) DNA Extraction Step

From each sample prepared as described above, DNAs were extracted in the same manner as that of Example 1, "1-3) DNA Extraction".

3. PCR Targeting Various Genes of *Listeria*

3-1) Amplification of Pathogenic Gene, *Listeria* Listeriolycin O (hlyA) Gene 3-1-1) Preparation of PCR Master Mix A master mix (total volume: 50 µl) of the following composition was prepared.

Ex-Taq® (Takara Shuzo, catalog number: RR001B, TaKaRa Ex Taq enzyme): 0.25 µl

10×Ex-Taq® Buffer (Takara Shuzo, catalog number: RR001B): 5 µl dNTP mixture (Takara Shuzo, catalog number: RR001B): 4 µl 5 pmol/µl SEQ ID NO: 7 (hlyA-F) DNA: 2.5 µl 5 pmol/µl SEQ ID NO: 8 (hlyA-R) DNA: 2.5 µl 2×SYBR® Green (cyanine dye) (BMA, catalog number: 50513): 10 µl Sterilized water: 15.75 µl Template DNA (15 ng/µl): 10 µl 3-1-2) PCR Thermal Cycle Profile for Amplification of hlyA Gene

TABLE 6

| Cycle | Repeats | Step | Retention time | Hold | Set (° C.) | Temperature elevation interval (° C.) |
|---|---|---|---|---|---|---|
| 1 | 1 | 1 | 03:00 | | 4 | |
| 2 | 1 | 1 | 00:30 | | 94 | |
| 3 | 50 | 1 | 00:20 | | 95 | |
| | | 2 | 01:00 | | 60 | |
| 4 | 1 | 1 | 03:00 | | 95 | |
| 5 | 350 | 1 | 00:08 | | 60 | 0.1 |
| 6 | | | | ∞ | 4 | |

3-1-3) PCR

Each of the DNA solutions prepared in 2-3) mentioned above was diluted to 15 ng/μl with TE buffer, and 10 μl of the diluted solution was used as a template DNA in 3-1-1) mentioned above. That is, 150 ng of the template DNA was contained in 50 μl of the PCR mixture. As a negative control, 10 μl of TE buffer was used.

According to the PCR thermal cycle profile shown in 3-1-2) mentioned above, PCR was performed by using a real-time PCR apparatus i Cycler® (Biorad, model number: iQ).

3-2) Amplification of 16S rRNA and 23S rRNA Genes 3-2-1) Preparation of PCR Master Mix A master mix (total volume: 50 μl) was prepared in the same manner as that of Example 3, 3-1) "Preparation of PCR master mix".

3-2-2) PCR Thermal Cycle Profile for Amplification of 16S rRNA Gene

The "PCR thermal cycle profile for amplification of 16S rRNA gene" mentioned in Example 3, 3-2) (Table 3) was applied.

3-2-3) PCR Thermal Cycle Profile for Amplification of Gram-Positive Bacterium 23S rRNA Gene The "PCR thermal cycle profile for amplification of gram-positive bacterium 23S rRNA gene" mentioned in Example 3, 3-3) (Table 5) was applied.

3-2-4) PCR

Each of the DNA solutions prepared in 2-3) was diluted to 15 ng/μl with TE buffer, and 10 μl of the diluted solution was used as a template DNA in 3-1-1) or 3-2-1) mentioned above. That is, 150 ng of the template DNA was contained in 50 μl of the PCR mixture. As a negative control, 10 μl of TE buffer was used.

According to the PCR thermal cycle profile shown in 3-2-2) or 3-2-3) mentioned above, PCR was performed by using a real-time PCR apparatus i Cycler® (Biorad, model number: iQ).

3-3) Agarose Gel Electrophoresis of PCR Amplification Product

Electrophoresis was performed in the same manner as that of Example 2, 1-4) "Electrophoresis of PCR amplification product". For the detection of the hlyA gene amplification product, 3% agarose gel was used.

4. Test Results

Figure 16:
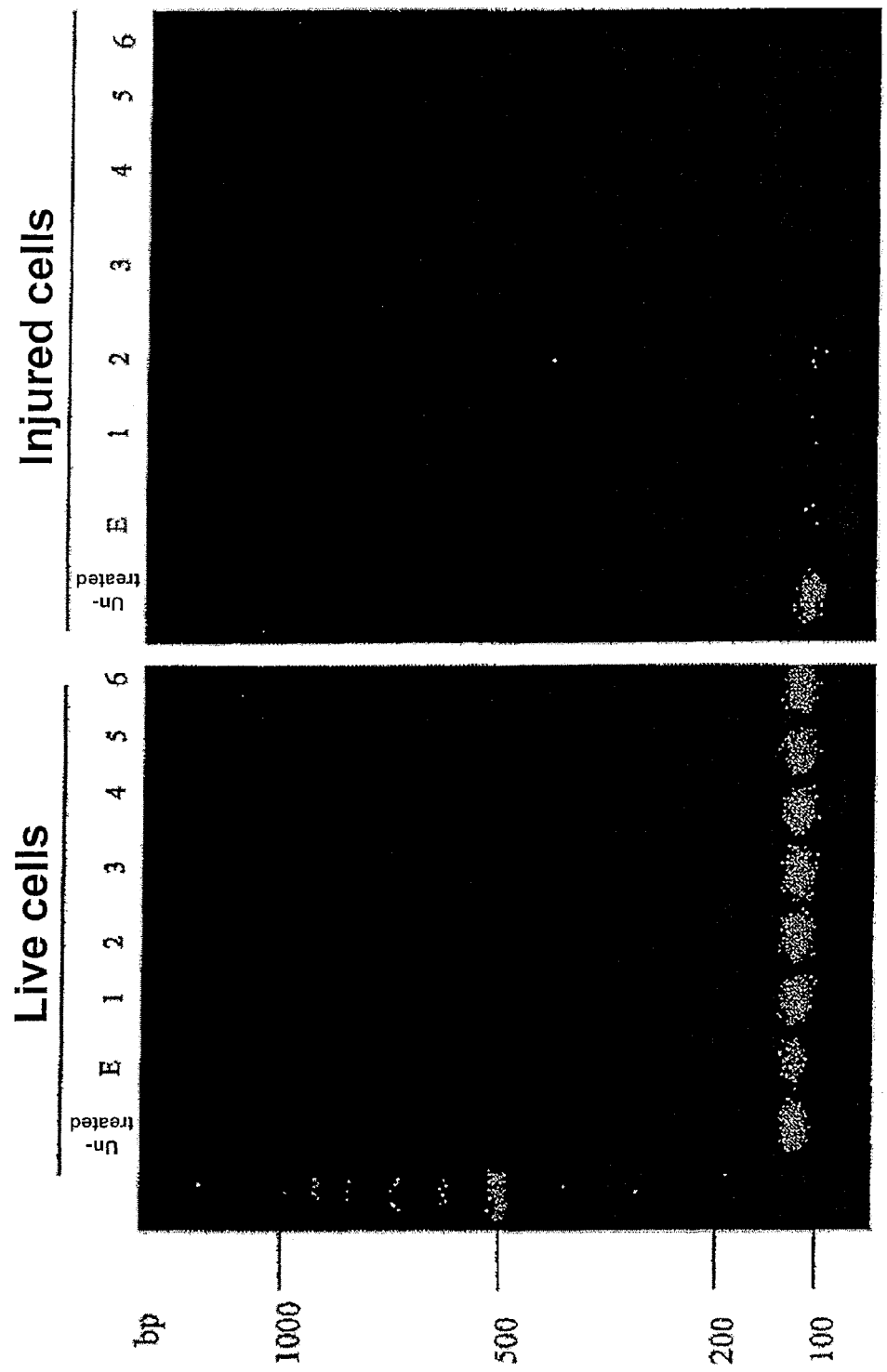
FIG. 16 Electrophoresis photographs showing results of PCR gene amplification targeting the hlyA gene of *Listeria* (live cells and injured cells) treated or not treated with EMA and then treated with a DNA gyrase poison or a topoisomerase poison:
Non: Untreated,
E: EMA
1: EMA/ciprofloxacin,
2: EMA/camptothecin,
3: EMA/etoposide,
4: EMA/ellipticine,
5: EMA/mitoxantrone,
6: EMA/amsacrine.
Figure 17:
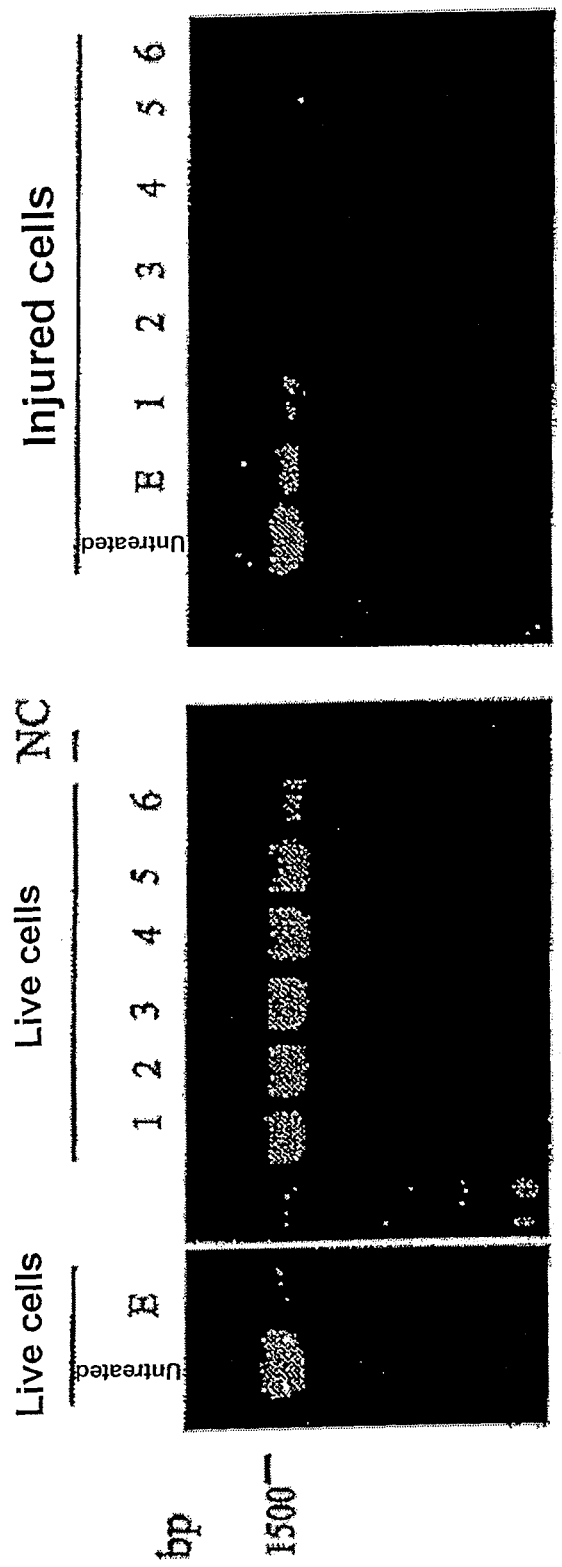
FIG. 17 Electrophoresis photographs showing results of PCR gene amplification targeting the 16S rRNA gene of *Listeria* (live cells and injured cells) treated or not treated with EMA and then treated with a DNA gyrase poison or a topoisomerase poison:
Non: Untreated,
E: EMA
1: EMA/ciprofloxacin,
2: EMA/camptothecin,
3: EMA/etoposide,
4: EMA/ellipticine,
5: EMA/mitoxantrone,
6: EMA/amsacrine.
Figure 18:
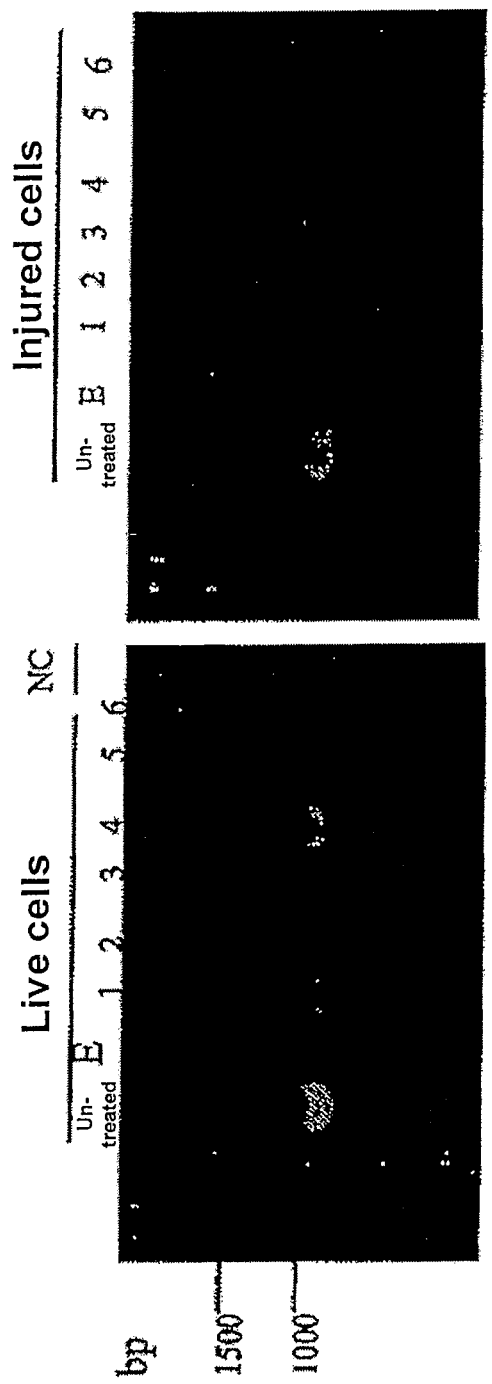
FIG. 18 Electrophoresis photographs showing results of PCR gene amplification targeting the 23S rRNA of *Listeria* (live cells and injured cells) treated or not treated with EMA and then treated with a DNA gyrase poison or a topoisomerase poison:
Non: Untreated,
E: EMA
1: EMA/ciprofloxacin,
2: EMA/camptothecin,
3: EMA/etoposide,
4: EMA/ellipticine,
5: EMA/mitoxantrone,
6: EMA/amsacrine.

The results for the case of targeting the hlyA gene are shown in FIG. 16, and the results for the case of targeting the 16S rRNA gene and the 23S rRNA gene are shown in FIGS. 17 and 18, respectively.

As seen from the results shown in FIGS. 16 and 17, when the hlyA and 16S rRNA genes were targeted, DNA amplification of the injured cells were only slightly inhibited by the EMA treatment. However, when a topoisomerase poison or DNA gyrase poison treatment was used together with the EMA treatment, the DNA amplification of the injured cells was further inhibited. In particular, by using etoposide, mitoxantrone or amsacrine together with EMA when the hlyA gene was targeted, and by using camptothecin, etoposide, ellipticine or amsacrine together with EMA when the 16S rRNA gene were targeted, the DNA amplification of the injured cells was markedly inhibited.

Moreover, as seen from the results shown in FIG. 18, when the 23S rRNA gene was targeted, PCR for the live cells was similarly markedly inhibited by using EMA and another topoisomerase poison or DNA gyrase poison.

When distinction of live cells from injured cells or dead cells is quickly performed with focusing a specific pathogenic bacterium, there is a tendency that it is more preferable to target a shorter gene region as short as 100 to 200 bp in order to enhance specificity for the pathogenic gene. It is considered that if the target region is so short as described above, the target region is not cleaved and amplified, even when EMA penetrates the cell walls of injured cells to cause cleavage of DNAs, and as a result, PCR is not suppressed completely. On the other hand, even if an extremely short hlyA gene of 113 bp was targeted, by using EMA and a topoisomerase poison or a DNA gyrase poison in combination, PCR for *Listeria* injured cells of a $10^8$ cfu/ml level was substantially completely inhibited, whereas PCR for live cells was not inhibited.

It is considered that this is because, for example, the topoisomerase poison randomly crosslinked DNAs at positions different from positions crosslinked by EMA to inhibit the religation among the cleavage and religation by still active intracellular DNA gyrase, bacterial topoisomerases I, III and IV of injured cells, and thereby provided a state that DNAs were cleaved everywhere in a more marked degree compared with the DNA cleaved state caused by EMA alone, resulting in cleavages even in the short target gene of 100 to 200 bp.

Therefore, it is possible to definitely distinguish live cells of a specific pathogenic bacterium from injured cells or dead cells thereof in a foodstuff or various clinical specimens containing background injured cells of the specific pathogenic bacterium at a high concentration. However, in order to suppress PCR amplification product for dead cells, it is preferable to add ATP and $Mg^{2+}$ as well as a topoisomerase or DNA gyrase (enzyme) beforehand, since the topoisomerase or DNA gyrase may be inactivated in dead cells, unlike injured cells.

For example, in expectoration of a tuberculosis patient administered with an anti-tuberculosis agent, which is a test specimen at a middle or later stage of treatment, *Mycobacterium tuberculosis* injured cells exist at a concentration of $10^8$ to $10^9$ cfu/ml due to the anti-tuberculosis agent. Even in such a case, live cells alone can be detected by the method to the present invention.

Reference Example 1

Preparation of Test Samples from Foodstuff

A method for preparing test samples will be exemplified below, assuming a case where a microorganism contaminates cow's milk as a foodstuff, one of test samples suitable for the method of the present invention.

To cow's milk, an EDTA solution was added at a final concentration of 1 to 5 mM, especially 2 mM, and Tween 80® (Polysorbate 80) was added at a final concentration of 0.1 to 0.5%, especially 0.1%, and the mixture was subjected to refrigerated centrifugation at 4° C. and 10,000×g for 10 minutes. It is preferable to add lipase (Sigma, E.C. 3.1.1.3) at a final concentration of 10 to 20 U/ml, allow the reaction at 30 to 37° C. for 30 minutes to 1 hour, then add proteinase K (Sigma, E.C. 3.4.21.64) at a final concentration of 20 U/ml and leave the mixture for 30 minutes to 1 hour. The surface lipid layer and the middle aqueous layer of the mixture were removed, and the precipitates were collected. The precipitates contain bacteria, somatic cells such as mammary epitheliocytes and bovine leucocytes, and when the mixture is centrifuged at 10,000×g or higher g, they further contain micellar protein degradation products (micellar casein incomplete degradation products) produced by incomplete degradation by proteinase K. The micellar casein incomplete degradation products are considered to consist of highly hydrophobic submicelles of α,β-casein.

Physiological saline of the same volume as the initial volume was added to the precipitates to form a suspension, the suspension was subjected to refrigerated centrifugation at 4° C. and 100×g for 5 minutes, and the supernatant containing microorganisms and the like was collected.

Reference Example 2

Preparation of Test Sample from Blood (1)

The same volume of physiological saline was added to heparinized blood, the mixture was subjected to centrifugation at 4° C. and 10,000×g for 5 minutes, the supernatant was removed, and the precipitates were collected. The precipitates contained bacteria, thrombocytes, mononuclear cells such as monocytes and lymphocytes, granulocytes and erythrocytes.

Reference Example 3

Preparation of Test Sample from Blood (2)

The same volume of physiological saline was added to heparinized blood, the mixture was subjected to refrigerated centrifugation at 4° C. and 100×g for 5 minutes to separate the mixture into plasma and hemocyte components (mononuclear cells such as monocytes and lymphocytes, granulocytes and erythrocytes), and the plasma containing microorganisms was collected.

Reference Example 4

Preparation of Test Sample from Blood (3)

The same volume of physiological saline was added to heparinized blood. In a sterilized test tube, Ficoll-Paque [Amersham Bioscience, 5.7 g/100 ml of Ficoll 400, 9 g/100 ml of sodium diatrizoate, specific gravity: 1.077 g/ml] of the same volume as that of the heparinized blood diluted twice was filled first, and the aforementioned heparinized blood diluted twice was slowly overlaid thereon with leaning the test tube aslant. Then, the layers were subjected to refrigerated centrifugation at 4° C. and 100×g for 5 minutes, and the supernatant containing microorganisms was collected. It is preferable to, before overlaying the heparinized blood diluted twice on Ficoll Paque, add a lipase (Sigma, E.C. 3.1.1.3) solution at a final concentration of 10 to 20 U/ml, then add 10 to 50 U/ml of a deoxyribonuclease I (Sigma, E.C. 3.1.21.1) solution, allow the reaction at 30 to 37° C. for 30 minutes to 1 hour, then add proteinase K (Sigma, E.C. 3.4.21.64) at a final concentration of 10 to 20 U/ml, and allow the reaction at 30 to 37° C. for 30 minutes to 1 hour.

Reference Example 5

Preparation of Test Sample from Blood (4)

To a sterilized test tube, Monopoly™ [Amersham Bioscience, mixture of Ficoil and Metrizoate, specific gravity: 1.115 g/ml] was added beforehand in ½ volume of heparinized blood, and heparinized blood was slowly overlaid thereon with leaning the test tube. Then, the layers were subjected to refrigerated centrifugation at 4° C. and 100×g for 5 minutes, and the supernatant containing bacteria was collected.

INDUSTRIAL APPLICABILITY

According to the present invention, live cells (Viable-and-Culturable state) of a microorganism contained in foodstuffs or clinical samples can be more selectively detected compared with dead cells (dead state) and injured cells (injured or Viable-but-Non Culturable state) by a quick method alternative to the culture method succeeding the characteristics of the culture method as they are.

What is claimed is:

1. A method for detecting live cells by distinguishing the live cells from dead cells and also from injured cells of microorganisms in a test sample, which comprises the following steps:
   a) treating the test sample with two poisons, wherein a first poison is a topoisomerase poison and a second poison is a DNA gyrase poison,
   b) extracting DNA from the test sample and amplifying a target region of the extracted DNA by PCR, wherein the length of the target region is 100 to 3000 nucleotides,
   c) analyzing a resulting PCR amplification product, and
   d) distinguishing the live cells from the dead cells and also from injured cells, wherein the method does not comprise treatment with ethidium monoazide.

2. The method according to claim 1, wherein the amplification product is analyzed by comparing the product to a standard curve representing the relationship between the amount of the microorganism and the amplification product, prepared by using standard samples of the microorganisms.

3. The method according to claim 2, wherein the PCR is performed by real-time PCR, and wherein the PCR and the analysis of the amplification product are simultaneously performed.

4. The method according to claim 1, wherein the test sample is selected from the group consisting of milk, a dairy product, a foodstuff produced from milk or a dairy product as a raw material, a blood sample, a urine sample, a spinal fluid sample, a synovial fluid sample and a pleural fluid sample.

5. The method according to claim 1, wherein the microorganism is a bacterium.

6. The method according to claim 5, wherein the target region is the 23S rRNA gene.

7. The method according to claim 6, wherein PCR is performed by using a primer set of the primers of SEQ ID NOS: 1 and 2, or a primer set of the primers of SEQ ID NOS: 3 and 4.

8. The method according to claim 1, wherein the microorganism is a pathogenic bacterium.

9. The method according to claim 8, wherein the target region is a pathogenic gene.

10. The method according to claim 9, wherein PCR is performed by using a primer set of the primers of SEQ ID NOS: 7 and 8.

11. The method according to claim 1, wherein the topoisomerase poison is selected from the group consisting of amsacrine, camptothecin, doxorubicin, ellipticine, etoposide, mitoxantrone, saintopin, topotecan and CP-115, 953.

12. The method according to claim 1, wherein the DNA gyrase poison is selected from ciprofloxacin, ofloxacin, enoxacin, pefloxacin, fleroxacin, norfloxacin, nalidixic acid, oxolinic acid and piromidic acid.

13. The method according to claim 1, wherein the following step is performed before step a):
   a') treating the test sample with a topoisomerase and/or a DNA gyrase.

* * * * *